US012138411B2

(12) United States Patent
Hvid et al.

(10) Patent No.: US 12,138,411 B2
(45) Date of Patent: Nov. 12, 2024

(54) INFLATION OF BALLOON IN BOWEL IRRIGATION SYSTEM

(71) Applicant: Coloplast A/S, Humlebaek (DK)

(72) Inventors: Niels Hvid, Vedbaek (DK); Jakob Duus Dolriis, Birkeroed (DK)

(73) Assignee: Coloplast A/S, Humlebaek (DK)

( * ) Notice: Subject to any disclaimer, the term of this patent is extended or adjusted under 35 U.S.C. 154(b) by 445 days.

(21) Appl. No.: 17/602,778

(22) PCT Filed: Apr. 3, 2020

(86) PCT No.: PCT/DK2020/050092
§ 371 (c)(1),
(2) Date: Oct. 11, 2021

(87) PCT Pub. No.: WO2020/207546
PCT Pub. Date: Oct. 15, 2020

(65) Prior Publication Data
US 2022/0152366 A1 May 19, 2022

(30) Foreign Application Priority Data

Apr. 11, 2019 (DK) .......................... PA 2019 70230

(51) Int. Cl.
*A61M 3/02* (2006.01)
*A61M 25/10* (2013.01)
(52) U.S. Cl.
CPC ........ *A61M 3/0202* (2021.05); *A61M 3/0258* (2013.01); *A61M 3/0295* (2013.01); *A61M 25/10181* (2013.11); *A61M 25/10184* (2013.11); *A61M 2205/3355* (2013.01)

(58) Field of Classification Search
CPC ...... A61M 3/02; A61M 3/0202; A61M 3/022; A61M 3/0225; A61M 3/0233; A61M 3/0237; A61M 3/0245; A61M 3/025; A61M 3/0254; A61M 3/0258; A61M 3/0262; A61M 3/0279; A61M 3/0283; A61M 3/0287; A61M 3/0295; A61M 31/00; A61M 5/142; A61M 5/48; A61M 25/10181; A61M 25/10184; A61M 2205/3355; A61M 2205/50; A61M 2205/502; A61M 2210/1067
See application file for complete search history.

(56) References Cited

U.S. PATENT DOCUMENTS

2018/0177937 A1* 6/2018 Eliasson ............. A61M 3/0202

FOREIGN PATENT DOCUMENTS

| CA | 3030143 A1 | 1/2019 |
|---|---|---|
| WO | 2016095929 A1 | 6/2016 |

* cited by examiner

*Primary Examiner* — Robert A Lynch
(74) *Attorney, Agent, or Firm* — Coloplast Corp., Coloplast A/S; Nick Baumann

(57) ABSTRACT

A method for inflating an inflatable balloon of a catheter for a bowel irrigation system includes initiating an inflation process in response to inputs provided by a user including inflating the inflatable balloon with a predefined volume of the liquid, assessing a static pressure inside the inflatable balloon, generating an output from the processor based on the static pressure, and controlling a feedback loop based on a difference between two consecutively assessed static pressures.

12 Claims, 8 Drawing Sheets

INFLATION OF BALLOON IN BOWEL IRRIGATION SYSTEM

The present disclosure relates to a method for inflating an inflatable balloon of a catheter for a bowel irrigation system.

BACKGROUND

Bowel irrigation is one of a number of treatments used to aid people with bowel problems. People suffering from bowel problems are often paralyzed, typically due to spinal cord injuries, and confined to a wheelchair or hospitalized. In these situations, often the peristaltic functions, i.e. the reflexes and muscles of the bowel, cannot be stimulated correctly. This results in constipation or random discharge of bowel contents. By using bowel irrigation, a stimulation of the peristaltic movements of the colon can be provided. To perform such bowel irrigation, a device comprising a catheter, also referred to as an anal catheter, anal probe, rectal catheter, or speculum, is provided. The catheter is inserted into the rectum through the anus. The catheter is typically retained in the rectum by retention means, most commonly a balloon, which is inflated against the wall of the rectum. A liquid, also referred to as an irrigation liquid, such as water or a saline solution, is then introduced into the rectum/bowels through the catheter. The amount of liquid is generally up to 1.5 liters, depending on the person. The introduced liquid stimulates the peristaltic movements of the bowel. After a specified period of time, such as 15 minutes, the catheter is removed, and the liquid, along with output from the bowel, is released through the anus.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
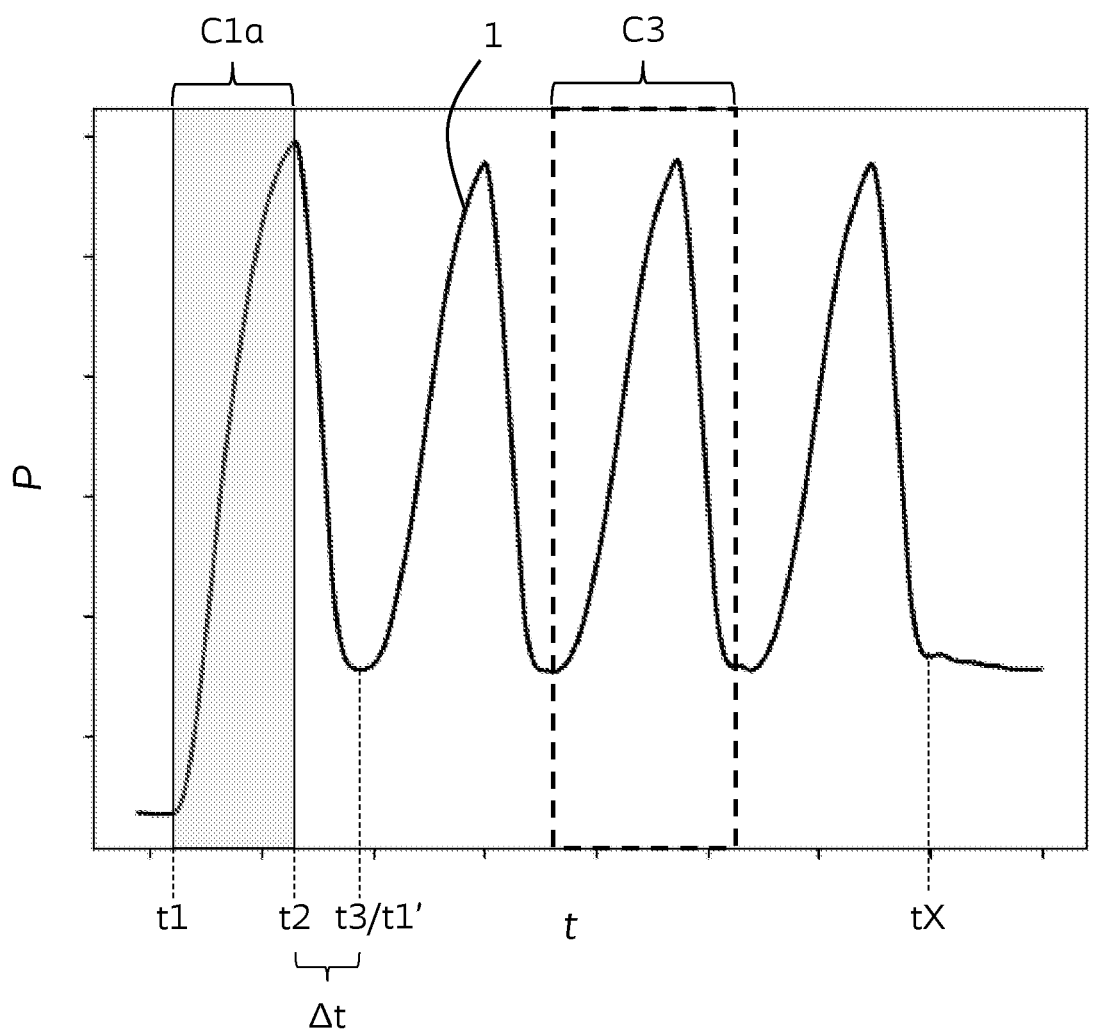
FIG. 1 illustrates the pressure inside a balloon as a function of time during an inflation process according to one embodiment of the invention.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The longitudinal direction is the direction from the distal to the proximal end. The transverse direction is the direction perpendicular to the longitudinal direction, which corresponds to the direction across the shaft of the catheter.

In the following, whenever referring to a bowel irrigation system or bowel irrigation, the referral to a system or method capable of irrigating the bowels of a user using a catheter. Commonly, the catheter is inserted through the anus. Bowel irrigation (systems) is also known in the art as anal irrigation (systems) and rectal irrigation (systems), and the terms may be used interchangeably in embodiments where the bowel irrigation system is adapted for use through the anus.

In the following, whenever referring to the bowel(s) of a user, the referral is to the intestines of the user. The referral can be to the lower intestines specifically, e.g. the rectum and/or the colon/large intestine. In the following, whenever referring to the rectum, the referral is to the terminal section/canal of the intestine ending in the anus. In the following, whenever referring to the anus, the referral is to the opening of the lower end of the alimentary canal, through which refuse of digestion is commonly excreted. In the following, whenever referring to anal, the referral is to a feature, device, method, or system pertaining to the anus, e.g. pertaining to engagement with or through the anus. In the following, whenever referring to the rectal walls, the referral is to the intestinal wall surrounding and defining the canal of the rectum.

In the following, whenever referring to a quantity, such as pressure, being in compliance with a threshold value, the referral is to the quantity being within the range where such quantity attains a desired value. Where the threshold value defines an upper limit to an acceptable value of the quantity, compliance is fulfilled whenever the value is equal to or below the threshold value. Likewise, where the threshold value defines a lower limit to an acceptable value of the quantity, compliance is fulfilled whenever the value is equal to or above the threshold value. Accordingly, non-compliance is used to describe the value of the quantity not being in compliance, i.e. falling outside the scope of compliance.

In the following, pressures are given in psi (pounds per square inch), where 1 psi=$7 \times 10^1$ mbar=7 kPa, and 1.0 psi=69 mbar=6.9 kPa, and 1.00 psi=68.9 mbar=68.9 kPa, and 1.000 psi=68.95 mbar=6.895 kPa.

The present disclosure provides a method for inflating an inflatable balloon of a catheter for a bowel irrigation system.

In a first aspect of the invention, the method for inflating an inflatable balloon of a catheter for a bowel irrigation system is disclosed. The bowel irrigation system comprises a container for holding a liquid, a catheter, a tubing connecting the container and the catheter, a pump, a control unit, and a pressure sensor. The catheter is adapted for being inserted into a rectum of a user and comprises an inflatable balloon. The pump is adapted for pumping liquid from the container to the balloon through the tubing. The control unit comprises a processor. The pressure sensor is in fluid communication with an interior of the inflatable balloon. The method comprises the steps of providing a liquid in the container and initiating an inflation process comprising a feedback loop comprising the steps of (i) inflating the balloon by a predefined amount of liquid, (ii) assessing a static pressure inside the balloon, and (iii) selecting an output based on the static pressure as assessed according to step (ii), the output being selected from restarting the feedback loop according to step (i), skipping step (i) and proceeding to assessing the static pressure according to step (ii), and terminating the feedback loop.

In the following, whenever referring to "inflation" or "deflation", the terms are related to inflation/deflation by a liquid, respectively. In the following, by inflation is meant the procedure of pumping liquid into a balloon, whereas by deflation is meant the procedure of withdrawing liquid from a balloon. Thus, deflation can be considered the opposite of/the counterpart to inflation, and vice versa.

The method as disclosed provides for a step-wise inflation of an inflatable balloon through the inflation process comprising a feedback loop, thereby facilitating a controlled inflation capable of reacting to physiological changes, such as peristaltic movements, or encounter with resistance, e.g. due to scar tissue or stool, during inflation. An output is to be considered an instruction to the feedback loop on how to proceed. In embodiments, the output is selected/generated by a processor comprised in the control unit and is based on certain inputs such as at least the static pressure as assessed in the preceding step. In embodiments, comparison means of the processor determines compliance of the input(s) with pre-determined threshold values and the processor selects an output based on compliance. In embodiments, the output is based on volume, bowel pressure, and/or time in addition to the static pressure as assessed in step (ii).

The method for inflating a balloon as disclosed provides a more controllable size of the balloon, as the method uses liquid for the inflation. Liquid is an incompressible fluid, and therefore the volume of the balloon is proportional to the volume of liquid provided. Moreover, overpressure inside the balloon due to compression is avoided, thus the risk for rupture of the balloon is minimized.

A bowel irrigation system is typically operated by the user themselves without the need of medical training or assistance by medical professionals. The irrigation is typically carried out in the user's own home and does not require a medical environment, such as a hospital. The irrigation may also be carried out as a fee-for-service in a commercial environment, which again does not require medical staff or a particular medical environment. The irrigation procedure is a relatively minor intervention, as compared to surgical or other procedures carried out by medical professional, and entails no substantial health risks when carried out by the user themselves with the required care and skill. Indeed, and as discussed herein, the inflation of the balloon by a liquid is a significant safety improvement in comparison to inflation by air.

In embodiments, the container can be any container suitable for holding a liquid. In embodiments, the container can be considered a reservoir. In embodiments, the container is capable of storing at least the amount of liquid required for an irrigation procedure or at least the amount of liquid required for an irrigation procedure and the amount of liquid required for inflating the balloon of the catheter. In embodiments, the liquid is water, such as tap water, or a saline solution. In embodiments, the liquid is an irrigation liquid for irrigating the bowels. In embodiments, the irrigation liquid is used to inflate the balloon as well. As such, the liquid can be referred to both an irrigation liquid and an inflation liquid, depending on the situation or use. In the following, irrigation liquid or inflation liquid is used to highlight the specific use of the liquid, but it should be understood that the irrigation liquid and the inflation liquid can be the same substance/material. In an embodiment, the container can comprise separate compartments; one for a required amount of irrigation liquid, and one for a required amount of inflation liquid.

In embodiments, the provision of liquid can be through a simple procedure of assessing the container, e.g. by removing a lid of the container, and pouring liquid into the container. In embodiments, a step of detecting presence of liquid in the container is equivalent to providing a liquid in the container. In embodiments, detection of the presence of liquid is effectuated by means of a sensor included in the container. In embodiments, providing a liquid in the container includes providing ample liquid, such that at least the balloon can be inflated by liquid in the container.

In embodiments, the catheter is adapted for insertion into a rectum of the user. One useful exemplary catheter comprises a main tubular part, typically called a shaft, extending from the distal end to the proximal end. A tip is positioned in the proximal end of the catheter and is provided as a rounded closed end of the shaft. In embodiments, the catheter comprises a connector in the distal end and may in an embodiment comprise a flared end of the catheter so that the diameter of the connector increases with respect to the tubular part. In particular, a proximal end of the catheter is configured for insertion into the rectum of the user. Usually, catheters used for bowel irrigation are typically 8-16 mm in external diameter, for example 10 mm. The length can be 70-200 mm, for example 150 mm. In embodiments, the catheter is of a size reflecting the needs or requirements of the user. As such, a range of different catheter sizes can be provided. In particular, catheter sizes denominated small and regular are used throughout the present disclosure. A small catheter has a smaller diameter than a regular catheter. For example, a small catheter can be suited for children, whereas a regular catheter can be suited for adults.

In embodiments the catheter is provided with eyelets in the proximal end, the eyelets communicating with an irrigation channel inside the catheter, so that irrigation liquid pumped into the catheter in a distal end can exit the catheter through the eyelets in the proximal end. Tests have shown that a diameter of the irrigation channel of approximately 3-7 mm, for example 4.3 mm, allows an adequate flow. The catheter is provided with an inflatable balloon for retaining said catheter inside the rectum during the irrigation procedure. Thus, the inflatable balloon can be considered a retention means. In embodiments, the balloon is suitable for sealing the anus, such that irrigation liquid cannot escape the rectum. In embodiments, the balloon extends radially around the catheter. In embodiments, the balloon when inflated resembles a torus encircling the catheter. The balloon can be considered expandable. In embodiments, the balloon is provided near the proximal end of the catheter. By extending radially around the catheter, the inflated balloon hinders the irrigation liquid from escaping the rectum through the anus (during the irrigation procedure). For the purpose of inflating the balloon, the catheter is provided with an inflation channel extending from the distal end of the catheter and terminating under the balloon, i.e. in the interior of the balloon. An adequate diameter of the inflation channel is approximately 1-4 mm, such as 2 mm. In an embodiment, the balloon is inflated with liquid, in particular with liquid held in the container. The balloon is inflated once the catheter is inserted in the rectum, and prior to introducing irrigation liquid to the rectum. The balloon is made of an elastic/flexible material. In embodiments, the balloon is made of a thermoplastic elastomer. Thereby, the balloon can expand and adapt to the internal shapes of the rectum, and thereby temporarily fixate the catheter in the rectum during the irrigation procedure.

In embodiments, the catheter is adapted for insertion by means of having an appropriate size, shape, and through an appropriate material choice. In embodiments, the method comprises the step of inserting the catheter into a rectum of a user. In embodiments, insertion of the catheter into the rectum is carried out manually by the user or by a health care professional. In embodiments, insertion is aided by the provision of a lubricant. In embodiments, insertion is aided by a certain surface treatment of the catheter reducing its friction. In embodiments, the catheter is inserted by a distance such that at least the entirety of the balloon is past an anal sphincter of the user, such as the internal anal sphincter.

In embodiments the balloon is inflatable by a nominal volume depending on the size of the catheter used (e.g. small and regular). By nominal is meant that the quantity (here, volume) is set by the system, and that the pump and/or other mechanisms of the system is adapted for complying with such nominal value. Thus, the nominal value is the value intended by the system. The volume of liquid in the balloon is related to its diameter, and as such reflects the needs and physical requirements of the user. In embodiments, for a regular size catheter, the balloon can be inflatable by a nominal volume of 20 ml, 40 ml, 60 ml, 100 ml, or 160 ml. In embodiments, for a small catheter, the balloon can be inflatable by a nominal volume of 12 ml, 26 ml, 40 ml, 60 ml, or 80 ml. A health care professional can assist the user in determining the optimal nominal volume, and as such the resulting size of the balloon. In embodiments, the nominal volumes are pre-determined and stored in a memory of the control unit. By specifying pre-determined volumes, the selection of an appropriate volume by a user is simplified, such as reduced to selecting from the range 0 (zero), XS, S, M, L, and XL, as explained below.

Table 1 summarizes exemplary sizes of the inflatable balloon (0-XL as selectable by the user) and the corresponding nominal volumes and diameters for a regular size catheter and a small size catheter. The indicated diameters are obtained in an experimental procedure of measuring the diameter following inflating the balloon by the indicated nominal volume. Thus, an uncertainty is attached to the diameters. Thus, the diameters should not be considered limiting for the invention. The diameter (10 mm) of the small and regular catheter for balloon size 0 (zero) reflects the basic diameter of the chosen catheter when the balloon is not inflated.

TABLE 1

| Balloon size | Regular | | Small | |
| --- | --- | --- | --- | --- |
| | Volume [ml] | Diameter [mm] | Volume [ml] | Diameter [mm] |
| 0 | 0 | 10 | 0 | 10 |
| XS | 20 | 26.5 | 12 | 23.6 |
| S | 40 | 37.6 | 26 | 34.6 |
| M | 60 | 45.1 | 40 | 42.1 |
| L | 100 | 54.2 | 60 | 49.5 |
| XL | 160 | 62.3 | 80 | 54.9 |

In embodiments the provision of a tubing connecting the container and the catheter allows for transfer of liquid from the container to selectably the balloon and the rectum, i.e. to the eyelets in the proximal end of the catheter and therefrom into the rectum once inserted. In embodiments, the tubing comprises a first and a second lumen, the first lumen connecting the interior of the balloon and the container, and the second lumen connecting the tip of the catheter and the container. In embodiments, the tubing is flexible. In embodiments, the tubing is transparent for providing visual assessment of the flow of fluid, i.e. both liquid and air, such as air arising from a rinsing procedure, where air is intentionally drawn into the tubing to avoid stagnant water.

In embodiments, a pump, such as an electrical pump, allows for the flow of fluid in the tubes, e.g. liquid intended for the inflation/deflation of the balloon and bowel irrigation, and air arising from a rinsing procedure. In embodiments, the pump is adapted for inflating the balloon by an amount of liquid, i.e. the pump is adapted for pumping (inflation) liquid from the container to the balloon. In embodiments, the pump is adapted for inflating and deflating the balloon. The amount of liquid can be as specified in table 1 above. In embodiments, the pump is adapted for pumping (irrigation) liquid from the container to the rectum through the catheter to irrigate the bowels. A system or ability for switching the pumping between pumping (irrigation) liquid into the rectum and inflating the retention means/balloon can be included in the irrigation system. In embodiments, two pumps are provided; one for pumping irrigation liquid into the rectum, and one for inflating the balloon of the catheter. The pump can be battery powered, such that the irrigation system is transportable and independent on provision of a power grid. The pump can be a gear pump or a centrifugal pump. In embodiments, the pump is a reversible electrical pump. In embodiments, the pump is able to pump air through the system in order to empty the tubing from liquid.

In embodiments, the control unit allows for the control of the flow of fluid generated by the pump. In embodiments, the control unit is adapted for controlling a flow of fluid in the system. For example, the control unit is provided at an appropriate position along the tubing. In embodiments, the control unit comprises a processor for generating/selecting outputs based on computations based on received inputs, e.g. inputs received from the pressure sensor, pump revolutions, and a pressure sensor pertaining to the pump pressure, i.e. an alternative pressure sensor capable of assessing the pressure generated by the pump. In embodiments, the control unit is provided with a memory. In embodiments, the control unit communicates with the interior of the tubing, such that the control unit can assess the fluid flowing within the lumens of the tubing. In embodiments, an electrical wiring is provided within and/or along the tubing for allowing an electrical connection between the pump and the control unit, such that the control unit can be used to control the performance of the pump and/or other parts of the irrigation system. In embodiments, an electrical wiring is provided between the catheter and the control unit, thereby providing electrical communication therebetween. In embodiments, the control unit and the pump are in communication through a wireless protocol. In embodiments, the control unit comprises a user interface for receiving inputs from the user, and a graphical user interface for presenting information to the user. In embodiments, the control unit comprises means for alerting the user, e.g. through haptic feedback, sound, or light. In embodiments, the control unit is capable of receiving one or more inputs, analyzing the one or more inputs, and selecting one or more outputs based on the analysis. In embodiments, selecting an output is equivalent to generating an output. Thus, according to the embodiment, selecting an output comprises a computational task of the system, wherein the inputs are analyzed, such as compared with one or more threshold values, in order to select an appropriate output.

In embodiments, the pressure sensor is adapted for assessing a pressure inside the balloon. In embodiments, assessing the pressure involves reading the pressure sensor and obtaining a numerical value. In embodiments, the pressure sensor is assessed/read by means of the processor. In embodiments, the assessed pressure is indicative of the pressure inside the balloon. In embodiments, the assessed pressure is referred to as the balloon pressure. In embodiments, the pressure sensor is in fluid communication with the interior of the balloon. In embodiments, the pressure sensor is arranged within the balloon, for example by being an integral part of the catheter. In an embodiment, the pressure sensor is arranged in the control unit. In embodiments, the pressure sensor is in fluid communication with the interior of the balloon through the first lumen. Thereby, the pressure can be assessed inside the first lumen connecting the interior of the balloon and the container. Due to the first lumen being in fluid communication with the interior of the balloon, the assessed pressure by the control unit is indicative of the pressure inside the balloon. Providing the pressure sensor in/by the control unit allows for an easier fabrication of catheters and/or for a simpler catheter construction. In embodiments, the control unit is adapted for assessing/reading the pressure sensor, such that said control unit can store and/or analyze the measurements/readings from the pressure sensor. Alternatively or additionally, the/a pressure sensor can be arranged where the tubing connects the pump. In embodiments, a secondary pressure sensor is in fluid communication with the irrigation channel of the catheter, such that the secondary pressure sensor is adapted for assessing the pressure in the irrigation channel, indicative of a bowel pressure. In embodiments, the bowel pressure is assessed continuously by the secondary pressure sensor in fluid communication with the irrigation channel of the catheter. In embodiments, a mathematical model is used to eliminate contributions from the balloon material in order to estimate the actual bowel pressure. In embodiments, assessing the bowel pressure and the balloon pressure simultaneously allows for monitoring the condition of the balloon of the catheter once the balloon has been inflated. Thus, a method for monitoring the condition of an inflated balloon of a catheter of a bowel irrigation system during an irrigation procedure of the bowels of a user can be established by the provision of a secondary pressure sensor in fluid communication with the irrigation channel of the catheter in conjunction with the pressure sensor adapted for assessing the pressure inside the balloon. In embodiments, such method of monitoring the condition of an inflated balloon comprises the steps of assessing a balloon pressure pertaining to the interior of the balloon, assessing a bowel pressure pertaining to the interior of the bowels, and calculating a differential pressure between the balloon pressure and the bowel pressure. In a typical situation of an inflated balloon during the irrigation pressure, the balloon pressure is greater than the bowel pressure, e.g. due to tension introduced by the balloon material. Thus, a certain differential pressure is present during the irrigation procedure. In the unlikely event that the balloon bursts during the irrigation procedure, such as due to a sudden increase of pressure exerted on the balloon, the differential pressure drops to zero (i.e. becomes negligible), since the pressure sensor originally in fluid communication with the interior of the balloon is now in fluid communication with the bowels. Thus, in embodiments, the bowel irrigation system is adapted for issuing a notification, e.g. in a user interface of the control unit, in the event of the differential pressure dropping to zero. In embodiments, the irrigation procedure is terminated in the event of detection of a burst balloon.

According to the first aspect of the invention, the method comprises the steps of providing a liquid in the container and initiating an inflation process comprising a feedback loop comprising the steps of (i) inflating the balloon by a predefined amount of liquid, (ii) assessing a static pressure inside the balloon, and (iii) selecting an output based on the static pressure as assessed according to step (ii). The output is selected from restarting the feedback loop according to step (i), skipping step (i) and proceeding to assessing the static pressure according to step (ii), and terminating the feedback loop. In embodiments, terminating the feedback loop is equivalent to not restarting the feedback loop, and as such can be considered the counterpart to the selectable output of restarting the feedback loop. As such, in embodiments, the output is selected from restarting the feedback loop according to step (i) and skipping step (i) and proceeding to assessing the static pressure according to step (ii). Thereby, the inflation process can be terminated by not selecting an output affecting a future loop of the feedback loop. In embodiments, routing the selected output to a relevant step of the feedback loop is implicitly contained in step (iii) when an output has been selected. In embodiments, routing the output to the relevant step of the feedback loop is included in a final step of the feedback loop. In embodiments, skipping step (i) and proceeding to assessing the static pressure according to step (ii) includes reassessing the static pressure and, according to step (iii), select an output based on the reassessed static pressure. Thereby, two assessments of the static pressure are made without being interrupted by the step of inflating the balloon by a predefined amount of liquid.

By initiating an inflation process comprising a feedback loop is meant that the system, such as the control unit, comprises pre-programmed instructions, which are to take effect as described, such as after providing a liquid in the container and inserting the catheter into the rectum of the user.

Due to this inflation process comprising a feedback loop, the inflation of the balloon by a predefined amount of liquid and the assessment of a static pressure inside the balloon are separated in time. Thereby, the pressure is assessed in a static phase of the liquid, where the volume in the balloon is stable/constant (static system), and as such the pressure is referred to as a static pressure. Thereby, the pressure assessment is less sensitive to a flow of liquid, i.e. a dynamic system, and the assessment can therefore be more reliable for certain uses. In embodiments, an assessment of the pressure can be considered a measurement of the pressure or a reading of the pressure.

The first step of the feedback loop includes inflating the balloon by a predefined amount of liquid. In other words, during the first step, a predefined amount of liquid is introduced/pumped into the balloon by means of the pump. In embodiments, the predefined amount of liquid is less than 40 ml, such as between 10 ml and 40 ml, or between 15 ml and 30, such as 20 ml. In embodiments, a maximum volume to be pumped into the balloon is specified in a step of the method prior to initiating the inflation process. In such a case, the predefined amount of liquid is less than such maximum volume. Thereby, the balloon cannot be fully inflated (reach the maximum volume) during a single inflation step. Instead, multiple loops of the feedback loop can be applied in order to reach the maximum volume. Once the balloon has been inflated by a predefined amount of liquid, the feedback loop proceeds to the second step. In embodiments, the pump is switched off when step (i) is fulfilled in each loop of the feedback loop.

During the second step of the feedback loop, the static pressure inside the balloon is assessed by means of the pressure sensor. In embodiments, the static pressure inside the balloon is measured by means of the pressure sensor. In embodiments, the assessed static pressure is indicative of the static pressure inside the balloon. The pressure inside the balloon depends on multiple factors. Such factors include the tension of the material of the balloon, the bowel pressure, a hydrostatic pressure, and a general pressure generated from inflating the balloon in a confined space (such as in the rectum of a user). By assessing the pressure inside the balloon following an inflation, the system receives an indication of the effect of introducing the predefined amount of liquid during the first step of the loop.

In embodiments, immediately following an inflation by a predefined amount of liquid, the liquid can be turbulent (dynamic pressure), which can disturb the pressure assessment. In embodiments, by separating the inflation and the assessment of the pressure inside the balloon by a predefined period of time, the pressure can be considered static. In embodiments, the predefined period of time is at least 1 second, such as 1 second, or at least 2 seconds, such as 2 seconds, or at least 3 seconds, such as 3 seconds.

The third step of the loop comprises selecting an output. In embodiments, the output is selected by means of the processor of the control unit. In embodiments, the output is based on the static pressure as assessed according to the second step of the loop. In embodiments, the output is based on a compliance check with one or more threshold values set on the static pressure, such as a first threshold value specifying a maximum static pressure allowed in the balloon and a second threshold value specifying a maximum allowed change of static pressure allowed from two consecutive assessments of the static pressure. In embodiments, the static pressure is considered an input, and the selected output specifies a future operating state of the feedback loop. In embodiments, the output is routed to the relevant step of the feedback loop to form a closed loop. In embodiments, the assessment of the static pressure inside the balloon (step (ii)) serves to predict, by means of the processor, the effect of a second inflation by a predefined amount of liquid. In embodiments, the processor can find, based on the pressure assessment, that an additional inflation (in a subsequent loop) may cause the balloon to exert an alarming counter pressure on the rectal walls or cause the bowel pressure to exceed what is considered safe. Thus, by means of the processor, an output can be selected specifying how the feedback loop should proceed. Thus, by providing a method for step-wise inflation of the balloon, it is possible to monitor such inflation and to abort/terminate the inflation process before health-related risks arises, or before risk of rupture of the balloon arises, due to a high pressure inside the balloon.

In embodiments, an output is based on the static pressure. In embodiments, the output is based on one or more inputs, the inputs including the static pressure, the relative change of static pressure, time, temperature, volume, and/or bowel pressure.

In embodiments, the output prompts restarting the loop. For example, such output can be selected when the processor based on compliance with pre-determined threshold values finds that further inflation can be considered safe and further inflation is necessary to reach the target volume. In embodiments, an output to restart the loop is default. Thereby, the loop automatically restarts unless otherwise prompted (e.g. by means of an output prompting termination or skipping step (i) and proceeding to an assessment of the pressure).

In embodiments, the output prompts pausing the feedback loop for a predetermined amount of time. For example, such output can be selected when the processor based on non-compliance with pre-determined threshold values finds that further inflation can constitute a risk for the user and/or risk of rupture of the balloon. In embodiments, a pause is a specified period of time wherein no further outputs are selected. For example, the pause allows for peristaltic movements to vanish and/or for the rectum to adapt to the balloon. In embodiments, a pause lasts for at least three seconds.

In embodiments, the output prompts skipping step (i) of the feedback loop and proceed to assessing the static pressure. In embodiments, the static pressure is reassessed in order to establish whether the reason for selecting the output to skip step (i) and reassess the pressure was justified (e.g. due to presence of stool or scar tissue) or whether the loop can restart. Presence of peristaltic movements can cause an increase of pressure inside the balloon. However, such peristaltic movements can vanish over time. Thus, by skipping step (i) and proceed to assessing the pressure, it can be found that further inflation according to step (i) can be considered safe because the reason for non-compliance (presence of peristaltic movements) has vanished in the meantime.

In embodiments, the output prompts terminating the feedback loop and as such the entire inflation process. Thus, terminating the feedback loop is equivalent to not restarting the feedback loop. For example, such output can be selected due to non-compliance with pre-determined threshold values (i.e. the pressure and/or change in pressure exceed relevant threshold values). In embodiments, the output of terminating the feedback loop is selected when the target volume has been reached. In embodiments, the output of terminating the feedback loop is selected when the pressure inside the balloon exceeds certain threshold values. In embodiments, the output of terminating the feedback loop succeed an output of skipping step (i) and assessing the static pressure, if such assessment finds that non-compliance remains.

In embodiments, the output prompting a termination of the feedback loop is selected if the bowel pressure exceeds a fourth threshold value. In embodiments, the bowel pressure is monitored continuously, e.g. with a sampling rate of higher than 1 Hz, or higher than 10 Hz. Thus, the feedback loop, and as such the inflation process, can be terminated in the event of an assessment of a bowel pressure exceeding the fourth threshold value. In embodiments, compliance of the bowel pressure with the fourth threshold value is checked continuously and in parallel with the inflation process by means of the processor. In embodiments, the fourth threshold value is 2 psi ($1\times10^2$ mbar), or 2.0 psi ($1.4\times10^2$ mbar), or 2.00 psi (138 mbar). In embodiments, the fourth threshold value is selected such as to prevent a bowel pressure exceeding 2 psi ($1\times10^2$ mbar), or 2.0 psi ($1.4\times10^2$ mbar), or 2.00 psi (138 mbar). Depending on how the secondary pressure sensor assessing the bowel pressure is arranged in the system, the fourth threshold value can be higher than an accepted maximum of 2 psi ($1\times10^2$ mbar), or 2.0 psi ($1.4\times10^2$ mbar), or 2.00 psi (138 mbar) inside the bowels. In embodiments, contributions not related to the actual bowel pressure is eliminated by means of the application of a mathematical model taking into account different contributions to the bowel pressure, including a hydrostatic pressure. Thus, in embodiments, the fourth threshold value is selected such that the actual bowel pressure does not exceed 2 psi ($1\times10^2$ mbar), or 2.0 psi ($1.4\times10^2$ mbar), or 2.00 psi (138 mbar).

In embodiments, the output of terminating the feedback loop is default. Thereby, it is ensured that inflation only occurs when the system is specifically prompted to do so (e.g. through selecting an output of restarting the feedback loop).

Due to surgery and/or radiation therapy, the rectal walls or underlying tissue can comprise scar tissue or rectal ulcers. In addition, the rectal walls can be sensitive following such treatment or due to use of medication. As such, a need exists to provide a cautious inflation process of a balloon of a bowel irrigation system, such that the balloon at no point exerts a too high pressure on the rectal walls or induces a bowel pressure exceeding regulatory limitations. The pressure inside the balloon is indicative of the pressure exerted on the rectal walls by the balloon and/or the induced bowel pressure. As such, by monitoring the pressure inside the balloon during inflation, it is possible to estimate the pressure exerted on the rectal walls or the induced bowel pressure, and thereby introduce means for alleviating risks related to hereto. In embodiments, the bowel pressure is assessed by means of the secondary pressure sensor. In embodiments, the bowel pressure forms basis for an output selectable in the third step of the feedback loop.

In embodiments, a series of assessments of the static pressure is made at a certain sampling rate during each step (ii) of the loop. Thus, during the second step of the loop, multiple assessments of the static pressure can be made. Such multiple assessments of the static pressure can be averaged to form the basis for the selection of an output.

In an embodiment, the method comprises the initial step of specifying a maximum volume and determining a current volume in step (ii) in addition to assessing a static pressure inside the balloon.

By an initial step is meant a step preceding the step of initiating the inflation process, and the specification of the maximum volume can therefore be made either before or after providing a liquid in the container. The maximum volume can be considered a target volume, thereby implying the intent to reach such volume. By a maximum volume is meant the intended/desired final volume of the balloon, assuming the inflation process has not been terminated beforehand. In embodiments, the maximum volume is the nominal volume of the balloon reflecting the needs and physical requirements of the user. Thus, the maximum volume reflects the desired final size of the balloon as selected by a health care professional and/or the user. Specifying a maximum volume can be through a user interface of the control unit.

According to the embodiment, the current volume in the balloon is determined in step (ii) of the feedback loop in addition to assessing a static pressure inside the balloon. For example, the current volume can be determined from the product of the number of times the balloon has been inflated according to step (i) of the feedback loop, and the amount of liquid contained in the predefined amount of liquid.

In embodiments, the current volume in the balloon is an input to the processor and an output can be selected based on the current volume. For example, an output based on the volume can be an output prompting to terminate the feedback loop, and as such the inflation process, because the volume in the balloon has reached the maximum volume as specified.

In an embodiment, the output of terminating the feedback loop is selected if the current volume in the balloon has reached the maximum volume.

In embodiments, the feedback loop is restarted, i.e. the loop starts over, until the maximum volume has been reached, in case no conflicting outputs have been selected. Thus, if the maximum volume is 100 ml and the predefined amount of liquid is 20 ml, the feedback loop is restarted five times in order to reach the maximum volume. Thus, five inflations and five assessments of the static pressure is made.

In embodiments, the output of terminating the feedback loop is selected only once the static pressure and/or the change of pressure exceed relevant threshold values, thereby allowing the balloon to reach any volume as long as relevant inputs are in compliance with their relevant threshold values. Thereby, the only limiting factor on the final size of the balloon is non-compliance with threshold values set on the static pressure and/or change of static pressure.

In an embodiment, the output of restarting the feedback loop is selected in step (iii) of the first loop of the feedback loop, thereby establishing two consecutively assessed static pressures. Thereby, the balloon is inflated at least twice by a predefined amount of liquid, and at least two assessments of a static pressure inside the balloon is made, before any other output is selected. Assessing the static pressure at least twice allows for the establishment of a trend in the static pressure over time and for the calculation of a relative change/difference between two consecutively assessed static pressures. In embodiments, the trend in the static pressure over time and/or the relative change between two consecutively assessed static pressures form basis for selecting an output according to step (iii) of the feedback loop.

In an embodiment, a difference between two consecutively assessed static pressures is calculated. By consecutively assessed is meant that the difference is calculated between the static pressure assessed in the current loop and the static pressure assessed in the preceding loop. For example, the calculation is made in step (iii) of a certain loop, where the static pressure assessed in the current loop refers to the static pressure as assessed in step (ii) of the same. The preceding loop refers to the loop immediately preceding the current loop. In embodiments, the difference is the absolute value of the calculated difference, i.e. the difference is non-negative.

In embodiments, the calculated difference is a relative change of the static pressure from the static pressure of the preceding loop and the static pressure of the current loop. In embodiments, a large relative change/difference is indicative of a sudden presence of resistance, e.g. stool or scar tissue, which needs to be considered when selecting an output. A sudden presence can also be indicative of peristaltic movements, and the selection of an output prompting skipping step (i) and proceed to (re-)assessing of the pressure can be beneficial in order to allow such peristaltic movements to vanish in the meantime.

In embodiments, the calculated difference forms basis for the selection of an output. In embodiments, the calculated difference is stored in a memory of the control unit.

In an embodiment, the selected output is based on the assessed static pressure of the current loop and the difference between two consecutively assessed static pressures. Selection of an output is provided for in step (iii) of the feedback loop as previously described. Thus, according to this embodiment, the processor uses the assessed static pressure of the current loop and the difference between two consecutively assessed static pressures to select an output. Thereby, the relative change in the static pressure forms basis for selecting an output in conjunction with the assessed static pressure according to step (ii).

In an embodiment, the output of restarting the feedback loop is selected if the assessed static pressure of the current loop is below or equal to a first threshold value and/or the difference between two consecutively assessed static pressures is below or equal to a second threshold value. Thus, the output prompting a restart of the feedback loop is conditional on two conditions, both of which are to be in compliance with relevant threshold values. According to the embodiment, the processor is to establish whether the assessed static pressure of the current loop, i.e. according to step (ii) of the loop, is below or equal to a first threshold value, and whether the calculated difference as defined above is below or equal to a second threshold value. The output is routed to step (i) of the feedback loop, causing the balloon to be inflated by a predefined amount of liquid. The output of restarting the feedback loop is selected based on a comparison of the assessed static pressure of the current loop and the calculated difference with pre-determined threshold values. In embodiments, the pre-determined threshold values are stored in a memory in communication with the processor. In embodiments, the output of restarting the feedback loop if the assessed static pressure of the current loop is below or equal to a first threshold value and the difference is below or equal to a second threshold value is selectable once the balloon has been inflated at least twice according to step (i) of the feedback loop.

In embodiments, the threshold values are selected such that compliance with the threshold values reflects that further inflation is considered safe, whereas non-compliance reflects that a too high resistance is met, e.g. due to an increased confinement of the balloon due to presence of stool, scar tissue, etc. In the case of non-compliance, an output of skipping step (i) and (re-)assess the static pressure or terminating the feedback loop can be selected. In embodiments, a large difference between the static pressure assessed in the current loop and the static pressure assessed in the preceding loop can indicate that the most recent inflation step (i.e. step (i) of the current loop) encountered a resistance, e.g. stool or scar tissue.

In an embodiment, the output of terminating the feedback loop is selected if the assessed static pressure of the current loop is above a first threshold value and/or the difference between two consecutively assessed static pressures is above a second threshold value. In embodiments, the first (second) threshold value is selected such that an assessed static pressure (change of static pressure) being equal to or below thereof is considered safe for further inflation, whereas an assessed pressure (change of static pressure) being above thereof indicates that further inflation may cause harm. A change of static pressure/difference between two consecutively assessed static pressures being above a second threshold value can indicate that the inflatable balloon has encountered resistance in the rectum, and that a further inflation can cause displacement of the origin of the resistance and/or potentially cause an increase of bowel pressure and/or exert an alarming pressure on the rectal walls. Thus, by introducing the output of terminating the feedback loop if the assessed static pressure of the current loop is above a first threshold value and/or the difference between two consecutively assessed static pressures is above a second threshold value provides a safety mechanism, whereby it is avoided that the above listed consequences of further inflation are effectuated.

In an embodiment, the output of skipping step (i) and proceeding to assessing the static pressure according to step (ii) is selected if the difference between two consecutively assessed static pressures is above a second threshold value. In embodiments, skipping (i) and proceeding to assessing the static pressure according to step (ii) is considered a reassessment of the static pressure, as no inflation according to step (i) has occurred in between the two assessments of the static pressure. In other words, the static pressure is reassessed if the difference between the static pressure assessed in the current loop and the static pressure assessed in the preceding loop is above a second threshold value. In embodiments, the reassessment of the static pressure is separated from the preceding assessment by a specified period of time, the period thereby constituting a pause. In embodiments, the specified period of time is between 1 second and 5 seconds, such as 3 seconds.

Instead of completely terminating the feedback loop, and as such the inflation process, if the assessed static pressure or change in static pressure (difference between two consecutively assessed static pressures) is in non-compliance with pre-determined threshold values, the static pressure is (re-)assessed before selecting an output of terminating the feedback loop. Thereby, the risk of false signals giving rise to an undesirable termination of the inflation process is reduced. In embodiments, false signals can arise due to system failure or due to temporary, peristaltic movements. Thus, a single assessment of the static pressure exceeding a threshold value can be due to the presence of temporary peristaltic movements, and it is therefore desired to provide a system capable of inflating an inflatable balloon within the rectum despite the presence of vanishing peristaltic movements, which may not pose a risk to the user. However, should the reassessment of the static pressure establish that the non-compliance was justified, an output of terminating the feedback loop can be selected, whereby the balloon is not inflated any further.

In embodiments, non-compliance with the first threshold value can likewise result in the selection of an output of skipping the first step and proceeding to assessing the static pressure. In embodiments, the output prompts reassessing the static pressure if the assessed static pressure of the current loop is above the first threshold value. Thereby, the absolute value of the static pressure forms basis for the selection of an output prompting skipping step (i) and (re-)assessing the static pressure.

In an embodiment, the output of terminating the feedback loop is selected if the difference between two consecutively assessed static pressures is above the second threshold value after reassessing the static pressure. Thus, the output of terminating the feedback loop is selected if the difference remains above the second threshold value following the effectuation of the output of skipping step (i) and proceeding to assessing the static pressure. If the difference between the static pressure assessed in the current loop and the static pressure assessed in the preceding loop is above the second threshold value after reassessing the static pressure, it may indicate a permanent presence of an object giving rise to an increased pressure (e.g. stool or scar tissue), rather than a temporary object (e.g. peristaltic movements). In such a case, according to the present embodiment, the output of terminating (i.e. not restarting) the feedback loop is selected, thereby terminating the entire inflation process. Thus, the inflation process can be terminated despite not having reached the specified maximum volume. In such cases, the final volume in the balloon becomes the product of the predefined amount of liquid and the number of times step (i) has been applied (i.e. how many times the balloon has been inflated by a predefined amount of liquid).

In embodiments, the output of terminating the feedback loop is selected if the assessed static pressure of the current loop is above the first threshold value after reassessing the static pressure. Thereby, the absolute value of the static pressure forms basis for selecting the output of terminating the feedback loop.

In an embodiment, the method further comprises the step of continuously assessing a pressure inside the balloon. Thereby, the pressure inside the balloon is monitored at all times during the inflation process, including during step (i) of the feedback loop, i.e. during inflation of the balloon by a predefined amount of liquid and during any intermediate periods. Thus, the assessment comprises both a dynamic pressure assessed during the inflation step of the feedback loop (step (i)) and the static pressure as previously described. By continuously is meant that the pressure inside the balloon is assessed with a sample rate of at least 1 Hz, or at least 10 Hz. Thereby, outputs can be selected based on the pressure inside the balloon notwithstanding the current step of the feedback loop. In embodiments, the step of continuously assessing a pressure inside the balloon runs in parallel with the feedback loop.

In an embodiment, the output of terminating the feedback loop is selected if the assessed pressure inside the balloon exceeds a third threshold value at any time during the inflation process. Thereby, the feedback loop can be terminated based on the pressure inside the balloon notwithstanding the current step of the feedback loop. Thus, if the pressure at any point in time exceeds the third threshold value, the feedback loop is terminated. In embodiments, the third threshold value is larger than the first threshold value, both of which relating to an absolute value of the pressure inside the balloon. During inflation, it is likely that the (dynamic) pressure is significantly higher than the static pressure, and the third threshold value is therefore selected such that such foreseen high dynamic pressures do not cause a termination unless a significantly high pressure is formed. However, should the dynamic pressure exceed the third threshold value, it can indicate sudden changes or presence of an object in the rectum giving rise to the increase of pressure. In such cases, the method is adapted to select the output of terminating the feedback loop, and as such the inflation process, on the basis of a pressure assessment regardless of the active/current step of the feedback loop.

In an embodiment, the predefined amount of liquid is nominally 20 ml. Thereby, the balloon is inflated by 20 ml during each loop of the feedback loop, in particular during step (i) of the feedback loop. Such volume provides for an expedient inflation without risking that an additional inflation of the balloon by such 20 ml increases the risk of exceeding any threshold values by an alarming magnitude. In embodiments, the final inflation by a predefined amount of liquid is adjusted if the maximal volume as specified is not an integer times the volume of the predefined amount of liquid.

In embodiments, the predefined amount of liquid is selected from the range between 10 ml and 50 ml, or between 15 ml and 30 ml, or between 15 ml and 25 ml, such as 20 ml.

In an embodiment, the predefined amount of liquid is reduced during each loop of the feedback loop. Thereby, a subsequent inflation by a predefined amount of liquid is less likely to cause any non-compliance with threshold values, since such subsequent inflation introduces less liquid into the balloon than what was inflated during the preceding loop. In embodiments, the initial (i.e. pertaining to the first loop of the feedback loop of the inflation process) predefined amount of liquid is 20 ml. In embodiments, the initial predefined amount of liquid is between 20 ml and 40 ml, such as 30 ml. In embodiments, subsequent inflation loop (step (i) of the feedback loop) introduce 1 ml less than the preceding loop, or 2 ml less than the preceding loop, or 3 ml less than the preceding loop, or 4 ml less than the preceding loop, or 5 ml less than the preceding loop. In embodiments, the subsequent inflation loop (step (i) of the feedback loop) introduces a volume being a fraction of the predefined amount of liquid of the preceding loop, such as between 50% and 99% of the preceding predefined amount of liquid, or such as 90% of the preceding predefined amount of liquid, or such as 80% of the preceding predefined amount of liquid, or such as 50% of the preceding predefined amount of liquid. As an example, in case the initial predefined amount of liquid is 20 ml, and the predefined amount of liquid is reduced by 80% during each loop of the feedback loop, the subsequent four loops inflate (in step (i)) the balloon by 16 ml, 12.8 ml, 10.2 ml, and 8.2 ml of liquid, respectively.

In an embodiment, the predefined amount of liquid is one Nth of the maximum volume, where N is an integer. Thus, the predefined amount of liquid fulfills the relationship $$V_1 = \frac{1}{N} V_{max},$$

where N is an integer, and where $V_1$ is the predefined amount of liquid and $V_{max}$ is the maximum volume. Thereby, the balloon can be inflated through a number of loops, where no final adjustment of the predefined amount of liquid is necessary to reach the maximum volume, i.e. no residual volume is left. For example, for a specified maximum volume of 100 ml, the predefined amount of liquid according to this embodiment can be 50 ml (N=2), or 33 ml (N=3), or 25 ml (N=4), or 20 ml (N=5), or 17 ml (N=6), and so forth. Thereby, the balloon can be inflated in a number of loops (e.g. 2 to 6 loops), where all loops (step (i) of the feedback loop) inflate the balloon by the same predefined amount of liquid (e.g. 50 ml, or 33 ml, or 25 ml, or 20 ml, or 17 ml, for a maximum volume of 100 ml), regardless of the maximum volume.

In embodiments, the integer N is between 2 and 20, such as 2, or 3, or 4, or 5, or 6, or 7, or 8, or 9, or 10, or 11, or 12, or 13, or 14, or 15, or 16, or 17, or 18, or 19, or 20. A large integer can be preferred when the specified maximum volume is large, whereas a small integer can be preferred when the specified maximum volume is small. Thereby, the predefined amount of liquid is adjusted to the maximum volume. Inflating the balloon by a small predefined amount of liquid during each loop (e.g. less than 20 ml, or less than 15 ml) can be beneficial for users having a particularly sensitive rectum, where particular caution must be exercised. By using a small predefined amount of liquid, the inflation process can take longer than using a large predefined amount of liquid. Using a large predefined amount of liquid (e.g. more than 20 ml, or more than 25 ml) can be beneficial for users not having a sensitive rectum and/or for speeding up the inflation process, whereby the system can quickly proceed with irrigating the bowels (the step of a bowel irrigation procedure following the inflation of the balloon as described herein).

In summary, the following situations are foreseen after a single assessment of the static pressure, i.e. during the first loop of the feedback loop:

The assessed static pressure is in compliance with the first threshold value, i.e. the static pressure in the balloon is equal to or below the first threshold value. In this situation, an output of restarting the feedback loop is selected. Thereby, a second loop is started.

The assessed static pressure is in non-compliance with the first threshold value, i.e. the static pressure in the balloon is above the first threshold value. In this situation, two outputs can be selected, depending on how the system is configurated. In a first case, an output of terminating the feedback loop is selected, i.e. equivalent to not selecting an output of restarting the feedback loop. In a second case, an output of skipping the first step and proceeding to assessing the static pressure is selected. Thereby, the (re-)assessed pressure forms basis for a new check of compliance. In case of compliance, an output of restarting the feedback loop can be selected. In case of persistent non-compliance, an output of terminating the feedback loop can be selected, thereby leaving the partly inflated balloon to serve as sufficient retention means for the subsequent irrigation procedure.

In summary, the following situations are foreseen after at least two assessments of the static pressure, i.e. once the feedback loop has been run at least twice:

The assessed static pressure is in compliance with the first threshold value and the difference between two consecutively assessed static pressures is in compliance with a second threshold value. In this situation, an output of restarting the feedback loop is selected. Thereby, a new loop is started.

The assessed static pressure is in non-compliance with the first threshold value and/or the difference between two consecutively assessed static pressures is in non-compliance with the second threshold value. In this situation, two outputs can be selected, depending on how the system is configurated. In a first case, an output of terminating the feedback loop is selected, i.e. equivalent to not selecting an output of restarting the feedback loop. In a second case, an output of skipping the first step and proceeding to assessing the static pressure is selected. Thereby, the (re-)assessed pressure forms basis for a new check of compliance with the first threshold value and/or second threshold value. In case of compliance, an output of restarting the feedback loop can be selected. In case of non-compliance, an output of terminating the feedback loop can be selected, thereby leaving the partly inflated balloon to serve as sufficient retention means.

If a maximum volume has been specified, check for compliance can be made, and similar outputs as those specified above can be selected depending on compliance/non-compliance. For example, if the maximum volume has been reached by the current volume in the balloon, the output of terminating the feedback loop is selected.

In embodiments, the output of terminating the feedback loop is selected in case the pressure—static and/or dynamic—is in non-compliance, i.e. exceeds, a third threshold value. During inflation, a dynamic pressure is assessed, and during the intervening period between two inflations, a static pressure is assessed. The pressure can be assessed continuously during the entire inflation procedure. Thereby, compliance with the threshold values can be checked continuously by the processor. By continuously is meant that the pressure sensor/processor has a sampling rate higher than 1 Hz or higher than 10 Hz.

DETAILED DESCRIPTION OF THE DRAWINGS

FIG. 1 illustrates a graph 1 depicting the pressure P inside a balloon as a function of time t during an inflation process in a situation where the balloon is inflated in a non-confined space. The inflation process comprises a feedback loop. The inflation process illustrated in graph 1 comprises four loops of the feedback loop, the third loop C3 being highlighted by a dashed box and a curly bracket for illustrative purposes. Each loop starts by the inflation of a predefined amount of liquid at time t1 as illustrated by a faded box and a curly bracket covering the first step (step (i)) C1a of the first loop.

During the inflation, the pressure increases, the pressure here being referred to as a dynamic pressure. Once the predefined amount of liquid, e.g. nominally 20 ml, has been pumped into the balloon, the pump is switched off/paused (or equivalent) at time t2 and the pressure in the balloon stabilizes for a predefined period of time Δt. At time t3, the pressure inside the balloon is assessed, the pressure now being referred to as a static pressure due to the stabilization of the pressure inside the balloon during the period Δt. A processor of the system selects an output prompting a future operating state of the feedback loop based on the assessed static pressure. In case the processor establishes that the assessed static pressure at time t3 is in compliance with relevant pre-determined threshold value(s), a new loop of the feedback loop is started at time t3, the new loop following the same procedure as described above in relation to the first loop, thus time t3 of the first loop is coinciding with time t1' of the second loop (assuming for illustrative purposes that the output is selected and routed to step (i) of the feedback loop instantaneously).

According to FIG. 1, four loops is applied before the inflation process is terminated at time tX. Termination can be a result of the volume inside the balloon having reached a specified maximum volume. For example, if the maximum volume has been set to 80 ml, each step (i) of each loop can have inflated the balloon by 20 ml of liquid.

Figure 2:
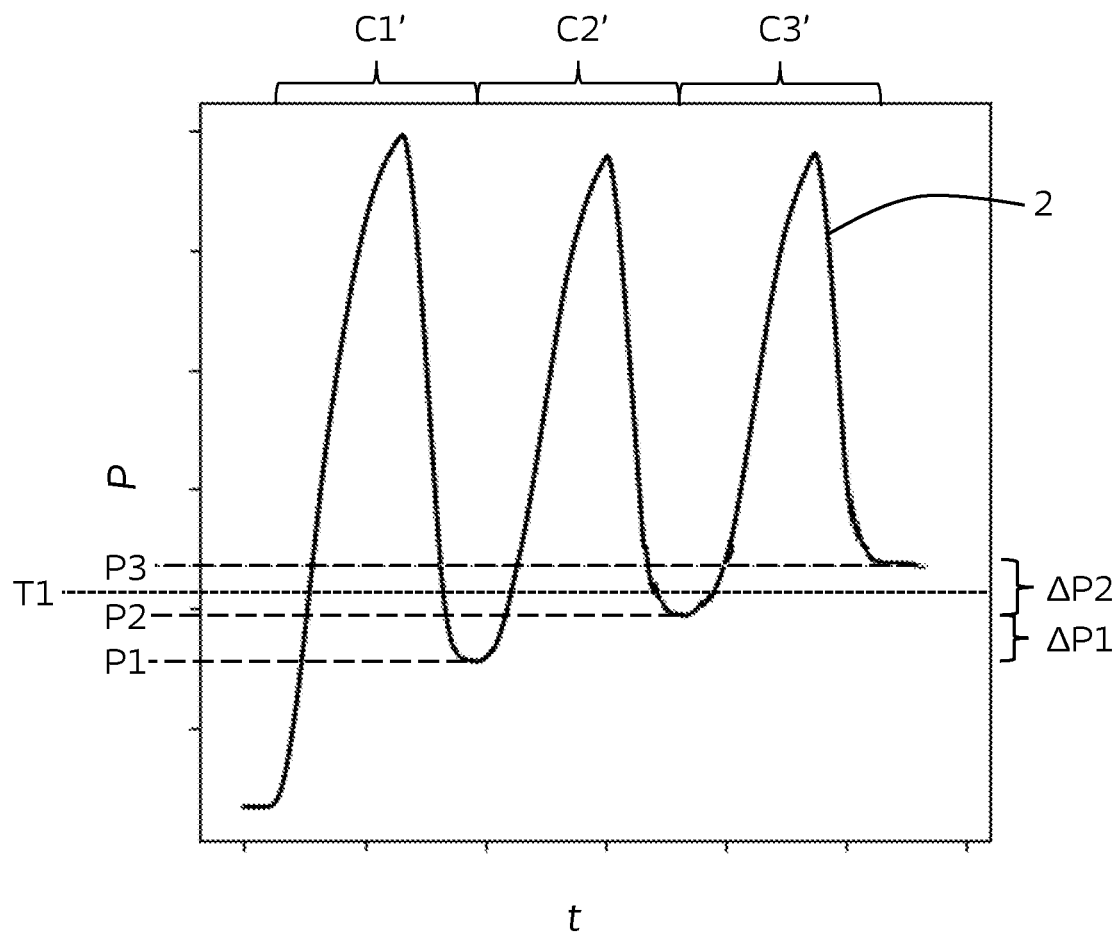
FIG. 2 illustrates the pressure inside a balloon as a function of time during an inflation process according to one embodiment of the invention.

FIG. 2 illustrates a graph 2 depicting pressure P as a function of time t in a situation where the balloon is inflated in a confined space. As illustrated by the increasing static pressures P1, P2, P3 over time, the confinement causes the static pressure inside the balloon to gradually increase during each of the three loops C1', C2', C3'. Such gradual increase of the static pressure indicates that the balloon meets resistance in its inflation, such as due to stool or scar tissue in the rectum. Neglecting such presence can cause a high counter pressure being exerted on the rectal walls by the balloon and/or an increasing bowel pressure, both of which potentially constituting a health risk for the user. According to an embodiment of the invention, a first threshold value T1 on the static pressure is applied. The first threshold value T1 specifies an upper value for the static pressure allowed in the balloon. Thus, exceeding (non-compliance with) the first threshold value T1 can potentially constitute a health risk. Therefore, the feedback loop can select an output of reassessing the static pressure or terminating the feedback loop/inflation process. As illustrated in FIG. 2, the assessed static pressure P1 of the first loop C1' and the assessed static pressure P2 of the second loop C2' are in compliance with the first threshold value T1 (the assessed static pressures are below the first threshold value T1). Compliance with the threshold value is checked after a stabilization period of the pressure and in case of non-compliance (i.e. the assessed static pressure being above the first threshold value T1), an output of terminating the feedback loop can be selected, such that the balloon is not inflated further, despite the maximum volume not having been reached. This situation is illustrated in FIG. 2 for the third loop C3', where the assessed static pressure P3 of the third loop C3' exceeds (is in non-compliance with) the first threshold value T1.

A second threshold value is applied to the relative change of the static pressure between the static pressure assessed in the current loop and the static pressure assessed in the preceding loop. Relative changes are illustrated in FIG. 2 by the first difference $\Delta P1$ between the assessed static pressure P1 of the first loop C1' ("the preceding loop" relative to the second loop C2') and the assessed static pressure P2 of the second loop C2 ("the current loop" when assessing the first difference $\Delta P1$), and the second difference $\Delta P2$ between the assessed static pressure P2 of the second loop C2 ("the preceding loop" relative to the third loop C3') and the assessed static pressure P3 of the third loop C3 ("the current loop" when assessing the second difference $\Delta P2$). A large difference/relative change can be indicative of a sudden resistance (e.g. due to stool or scar tissue), and as such, further inflation can potentially constitute a health risk.

Figure 3:
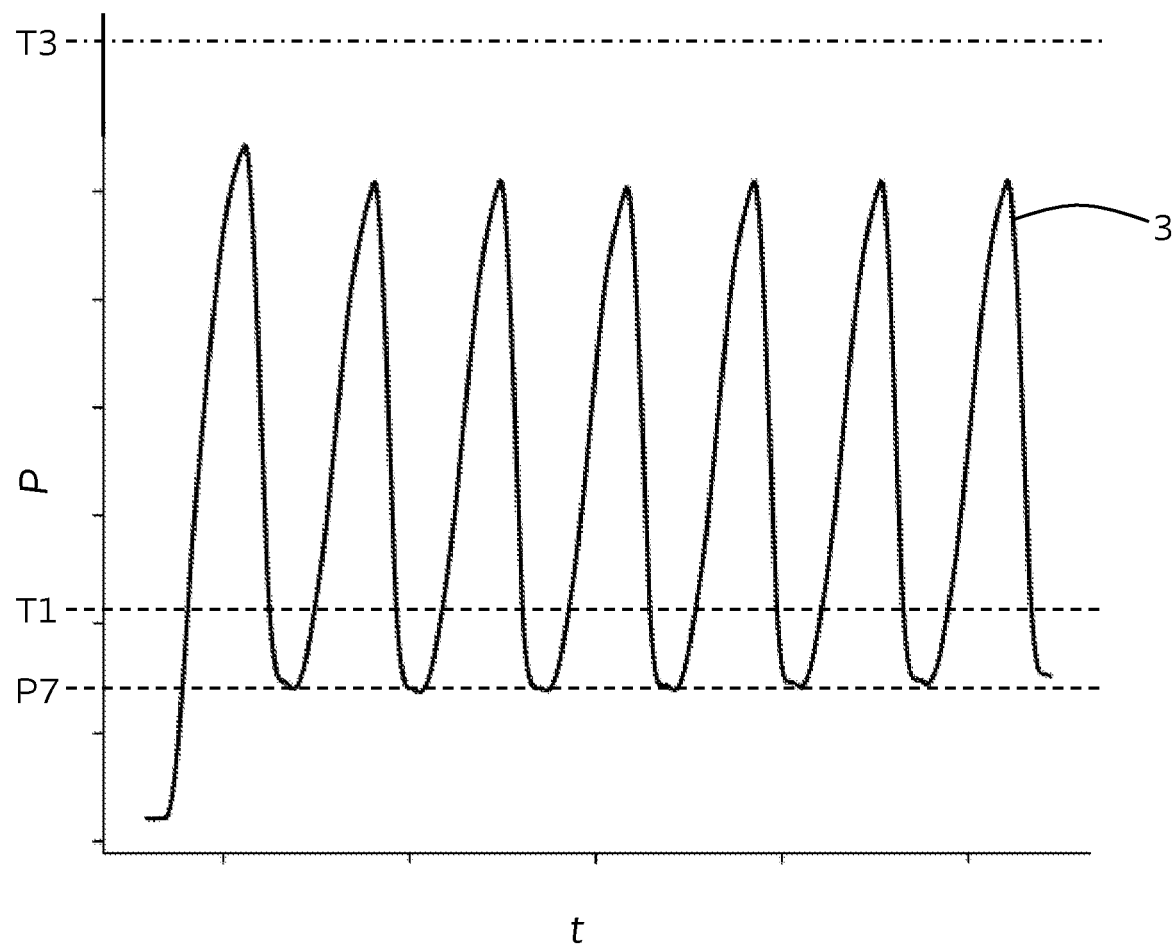
FIG. 3 illustrates the pressure inside a balloon as a function of time during an inflation process according to one embodiment of the invention.

FIG. 3 illustrates a graph 3 depicting pressure P as a function of time t for an inflation process comprising seven loops. The assessed static pressures P7 for each of the seven loops are similar in magnitude and in compliance with the first threshold value T1. Thus, no significant change in static pressure between the loops is observed in FIG. 3. A third threshold value T3 is included in the figure, the third threshold value T3 limiting the maximum allowed pressure inside the balloon at any time. Since the pressure during none of the seven loops neither exceed the third threshold value T3 nor is in non-compliance with the first T1 or second threshold value, a loop is restarted after each assessment of a static pressure until the maximum volume is reached after seven loops.

Figure 4A:
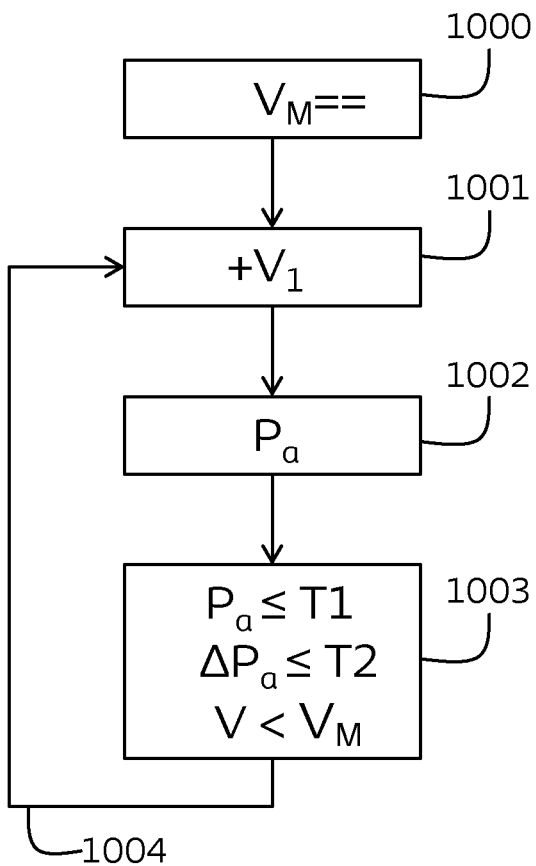
FIG. 4A illustrates a flowchart of an inflation process according to one embodiment of the invention.

FIG. 4A illustrates a flowchart of a method for inflating an inflatable balloon. The method comprises an initial step 1000 of specifying a maximum volume "$V_M$=" and a feedback loop comprising three steps 1001, 1002, 1003. In embodiments, specifying a maximum volume is optional, and in case no maximum volume is specified, the feedback loop can restart until non-compliance with one or more threshold values causes an output of terminating the feedback loop to be selected. In the following, it is assumed that a maximum volume has been specified, such that compliance with such maximum volume is checked.

In the first step 1001 of the feedback loop, the balloon is inflated by a predefined amount of liquid "+$V_1$". In the second step 1002, the static pressure $P_a$ (alternatively stylized as P_a) inside the balloon is assessed by means of a pressure sensor in fluid communication with the interior of the balloon, and a processor communicating with the pressure sensor. The first step 1001 and the second step 1002 can be separated by a predefined period of time, ensuring a static state of the liquid in the balloon upon pressure assessment, such that the assessed pressure can be considered a static pressure. The third 1003 step is handled by a processor and take the assessed pressure $P_a$ of the second step 1002 as an input. In the third step 1003, the processor performs a comparison of the assessed static pressure $P_a$ with a first threshold value T1 and determines whether the assessed pressure $P_a$ is in compliance with the first threshold value T1, i.e. whether $P_a \leq T1$ is true. Additionally, provided at least two loops have been made, the processor calculates a difference $\Delta P_a$ (i.e. the relative change) between the static pressure $P_a$ assessed in the current loop, i.e. in the second step 1002 of the current/active loop, and the static pressure assessed in the preceding loop. The processor performs a comparison of the calculated difference $\Delta P_a$ with a second threshold value T2 and determines whether the calculated difference is in compliance with the second threshold value, i.e. whether $\Delta P_a \leq T2$ is true. Finally, it is checked whether the current volume V in the balloon is less than the target volume $V_M$, i.e. whether $V < V_M$ is true. In the example of FIG. 4A, all conditions are met, and the processor therefore selects an output of restarting the loop, i.e. to inflate the balloon by predefined amount of liquid +$V_1$ and proceed through the steps as described above. The selected output is routed to the first step 1001 of the feedback loop through the route 1004. In embodiments, the pressure inside the balloon is monitored during the entire inflation process, including during the first step 1001. Thus, a check for compliance with a third threshold value can be made in with the feedback loop, where non-compliance can result in an output prompting a termination of the feedback loop to be selected.

Figure 4B:
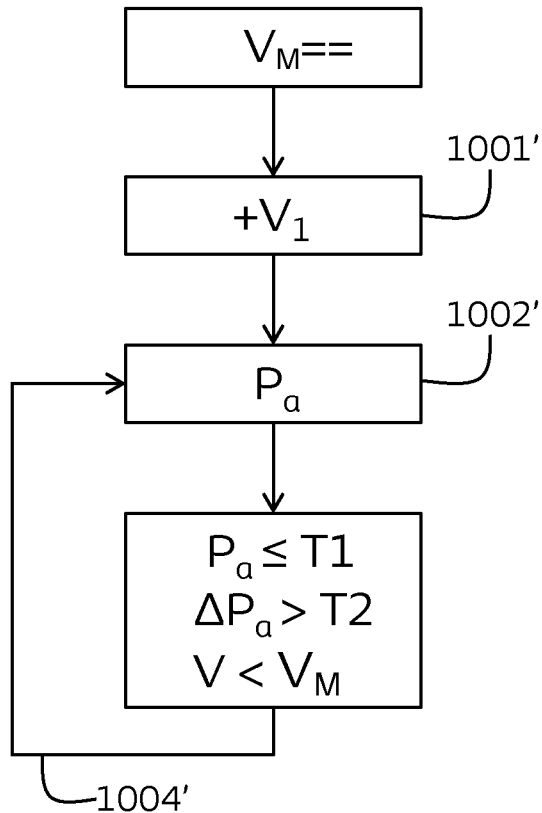
FIG. 4B illustrates a flowchart of an inflation process according to one embodiment of the invention.

FIG. 4B illustrates a flowchart similar to FIG. 4A, as described above, but where non-compliance with the second threshold value T2 is found, i.e. $\Delta P_a > T2$. In this case, the processor selects an output of skipping the first step 1001' (step (i)) and proceeding to assessing the static pressure $P_a$ in the second step 1002' (step (ii)) before selecting a subsequent output, e.g. whether to restart the feedback loop from step (i) or to terminate the feedback loop. The output of skipping the first step 1001' and proceeding to assessing the static pressure is routed to the second step 1002' as illustrated by the route 1004'. Skipping the first step 1001' can be considered a reassessment of the static pressure. Non-compliance with the second threshold value T2 could be due to the presence of vanishing peristaltic movements, and by reassessing the pressure $P_a$ again after a short period of time, e.g. less than 3 seconds, it may be found that compliance is re-established, and the feedback loop can proceed as described in relation to FIG. 4A. In case non-compliance is persistent, an output of terminate the feedback loop can be selected. Terminating the feedback loop is equivalent is equivalent to not restarting the feedback loop, and as such to terminating the inflation of the balloon. Termination of the feedback loop results in a balloon comprising less liquid than what was originally intended when setting the maximum volume. When terminating the feedback loop before the maximum volume has been reached, the current volume in the balloon serves as the retention means of the catheter during the subsequent irrigation procedure.

If it is found that the current volume V in the balloon is greater than the difference $V_M - V_1$, the method/system can adapt (reduce) the volume of the predefined amount of liquid in the last inflation step to comply with, and reach, the maximum volume and not over-shooting. Thus, by predefined is meant that the volume can be adjusted from loop to loop, but in such a way, which is allowed by, or is a result of, computations made by the processor. Thus, the processor is allowed to compute and potentially change the predefined amount of liquid during each loop of the feedback loop. For example, if the maximum volume $V_M$ is 90 ml, $V_1$ is 20 ml, and the current volume in the balloon is 80 ml, the processor can adjust the volume of the predefined amount of liquid for the final loop to 10 ml, thereby reaching the maximum volume. However, in embodiments, the maximum volume can be selected to be an integer times the predefined amount of liquid, thereby circumventing the need for adjustment. Correspondingly, the predefined amount of liquid can be selected to be one Nth of the maximum volume, where N is an integer.

Figure 5A:
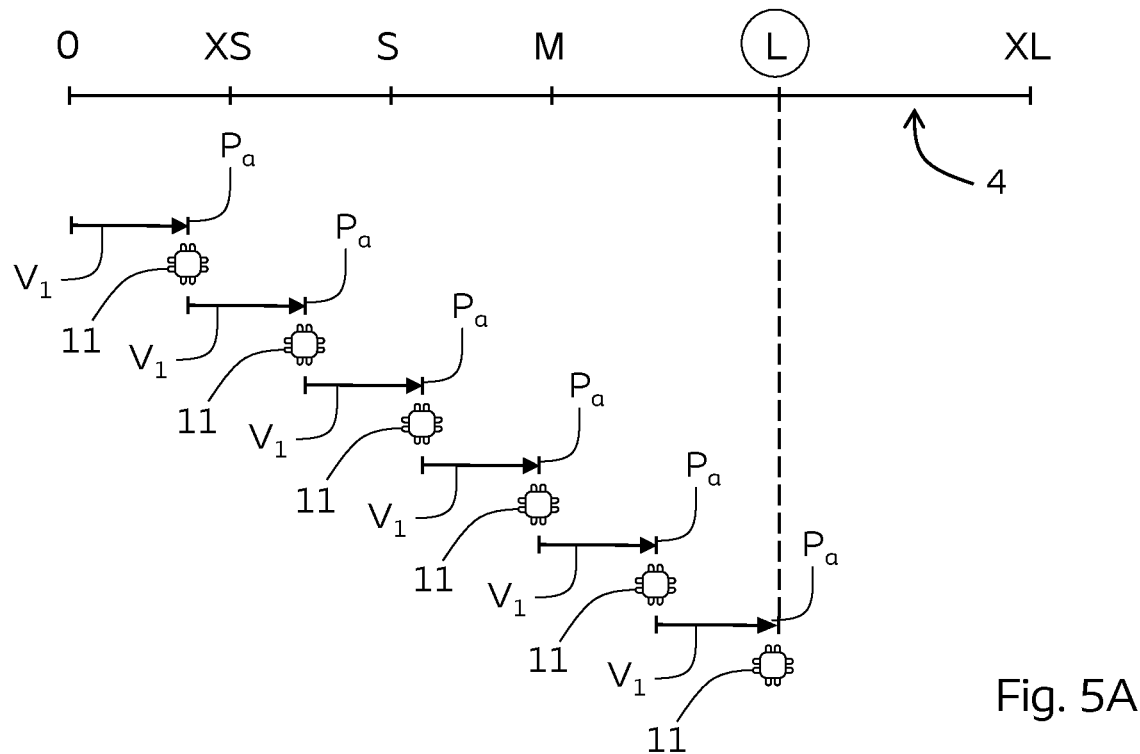
FIG. 5A illustrates a volumetric scale visualizing an inflation process according to one embodiment of the invention.

FIG. 5A illustrates a volumetric scale 4 visualizing an inflation process according to the invention. In the present example, a maximum volume of "L" (Large) has been specified/selected. The inflation process according to an embodiment of the invention comprises a feedback loop comprising a first step of inflating the balloon by a predefined amount of liquid $V_1$ being less than the maximum volume. Once the balloon has been inflated by the predefined amount of liquid $V_1$, the static pressure inside the balloon is assessed $P_a$ and a processor 11 of the system carrying out the method selects an output based on the static pressure. If it is found that the assessed static pressure $P_a$ is in compliance with at least one threshold value, such as a first threshold value limiting the maximum allowed static pressure, an output of restarting the feedback loop is selected, thereby inflating the balloon by a predefined amount of liquid $V_1$ again. In case of compliance with the at least one threshold value during the entire inflation process, the amount of liquid in the balloon eventually reaches the maximum volume and an output of terminating (not restarting) the feedback loop is selected.

Figure 5B:
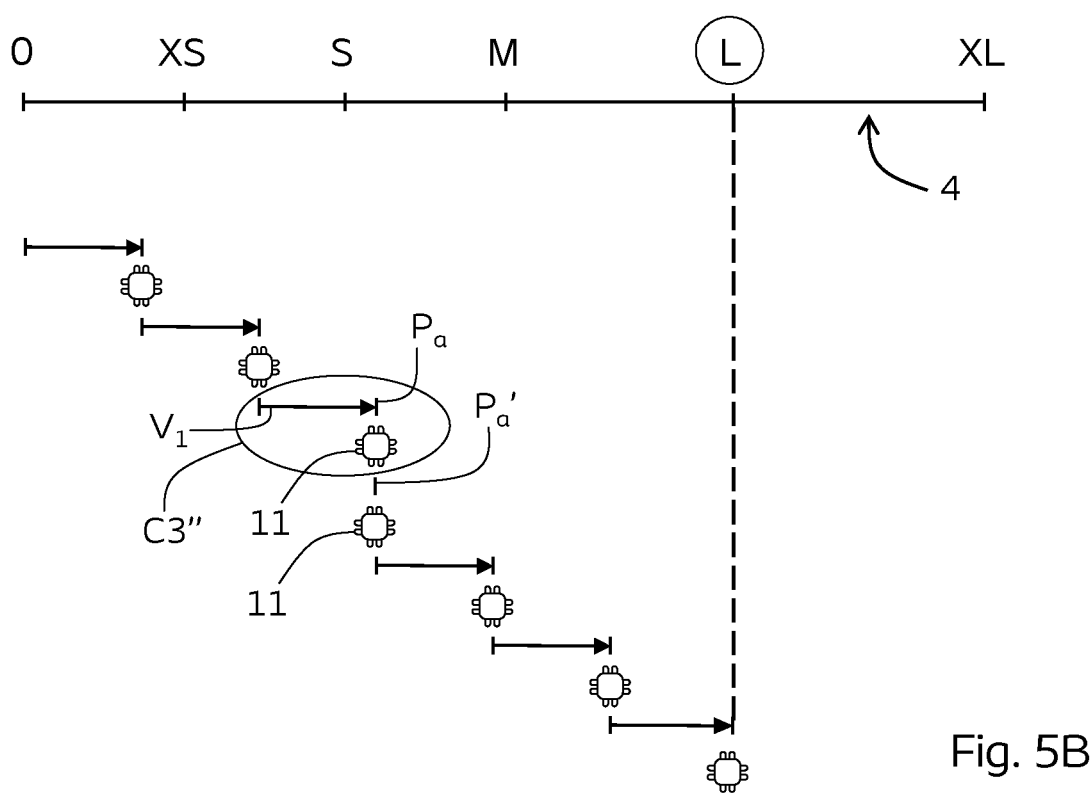
FIG. 5B illustrates a volumetric scale visualizing an inflation process according to one embodiment of the invention.

FIG. 5B illustrates a volumetric scale 4 similar to the one of FIG. 5A. In FIG. 5B, an inflation process according to the invention is visualized in a situation where non-compliance is established in the third loop C3". Non-compliance can be due to the difference between two consecutively assessed static pressures exceeding a second threshold value. In this situation, an output of skipping the first step (step (i)) and thereby reassessing $P_a$' the static pressure is selected, and the reassessed pressure $P_a$' forms basis for a new output selected by the processor 11. As illustrated by a new series of loops/inflations, compliance with the second threshold value is reestablished, and an output selected by the processor 11 prompts restarting the feedback loop. Eventually, the series of inflations, one for each loop, causes the volume in the balloon to reach the maximum volume.

Figure 6:
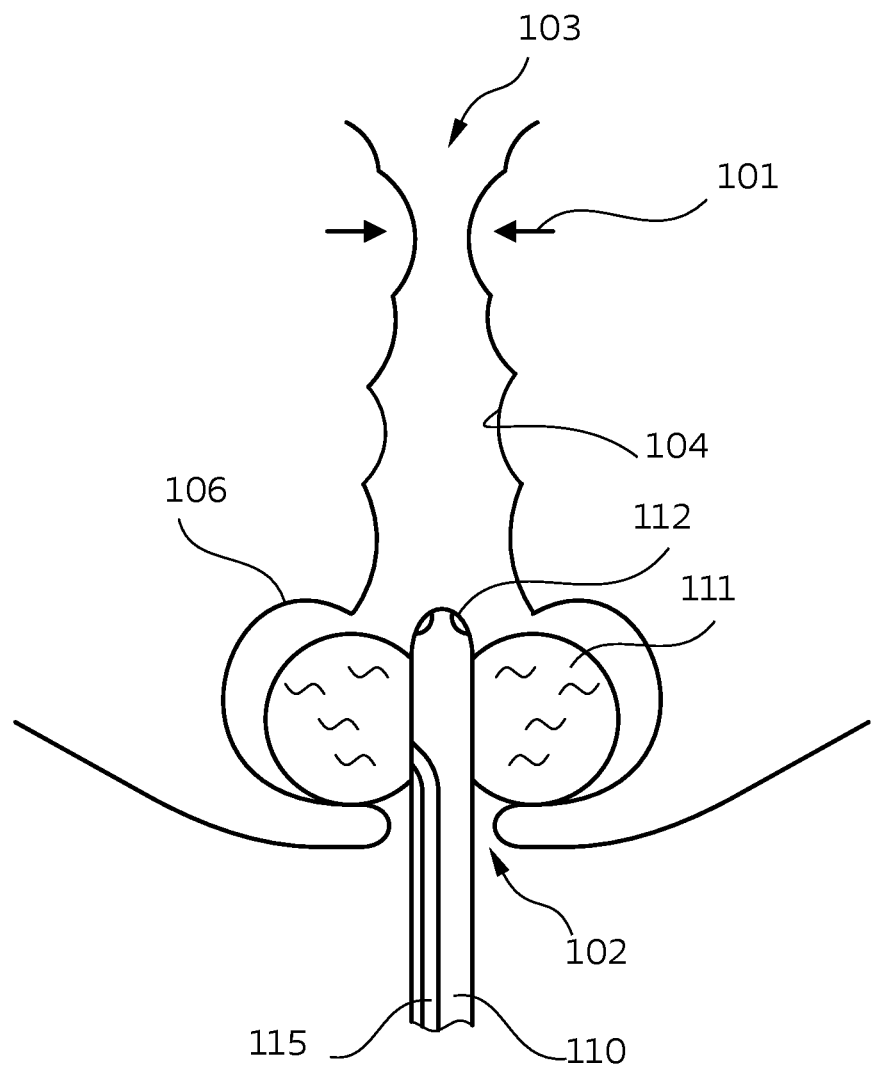
FIG. 6 illustrates a cross-sectional view of a rectum and one embodiment of a catheter of a bowel irrigation system.

FIG. 6 illustrates a cross-sectional view of a rectum 103 of a user and a catheter 110 of a bowel irrigation system inserted herein through the anus 102. The catheter 110 comprises an inflatable balloon 111, inflatable through the inflation channel 115. The inflation channel 115 is in fluid communication with a container holding the liquid used for inflating the balloon 111. The inflatable balloon 111 is considered a retention means for retaining the catheter 110 in a fixed position inside the rectum 103 and further serves blocking the anus 102 during the irrigation procedure. The proximal end of the catheter 110 is provided with eyelets 112 communicating with an irrigation channel (not shown) inside the catheter 110, so that liquid pumped into the catheter 110 in its distal end can exit the catheter through the eyelets 112 at the proximal end and enter the rectum 103. The liquid can be held in a container in fluid communication with the irrigation channel. In the lower part of the rectum 103, a chamber 106 is naturally present, the chamber 106 allowing the inflatable balloon 111 to be inflated without pushing excessively on the rectal walls 104. Once the inflatable balloon 111 has been inflated inside the chamber 106, irrigation liquid can be pumped into the rectum 103 through the catheter 110 and further through the eyelets 112. During such procedure, and during the subsequent procedure of letting the irrigation liquid stimulate the bowels for a specified period of time, peristaltic movements 101 may arise. A peristaltic movement can be defined as a radially symmetric contraction and relaxation of muscles propagating a wave. Thus, the peristaltic movement 101 can propagate towards the anus 102 and eventually exert a pressure on the balloon 111 inflated by an (incompressible) liquid. Due to the incompressible nature of liquids, the exerted pressure can cause a counter pressure on the rectal walls 104 and as such potentially constitute a health risk for the user. For example, the specified period of time during which the irrigation liquid is left to stimulate the bowels is between 1 minute and 30 minutes, for example for 15 minutes. During this period, the catheter 110 is kept in place inside the rectum and the balloon 111 is kept inflated to prevent the irrigation liquid to escape through the anus 102.

Figure 7:
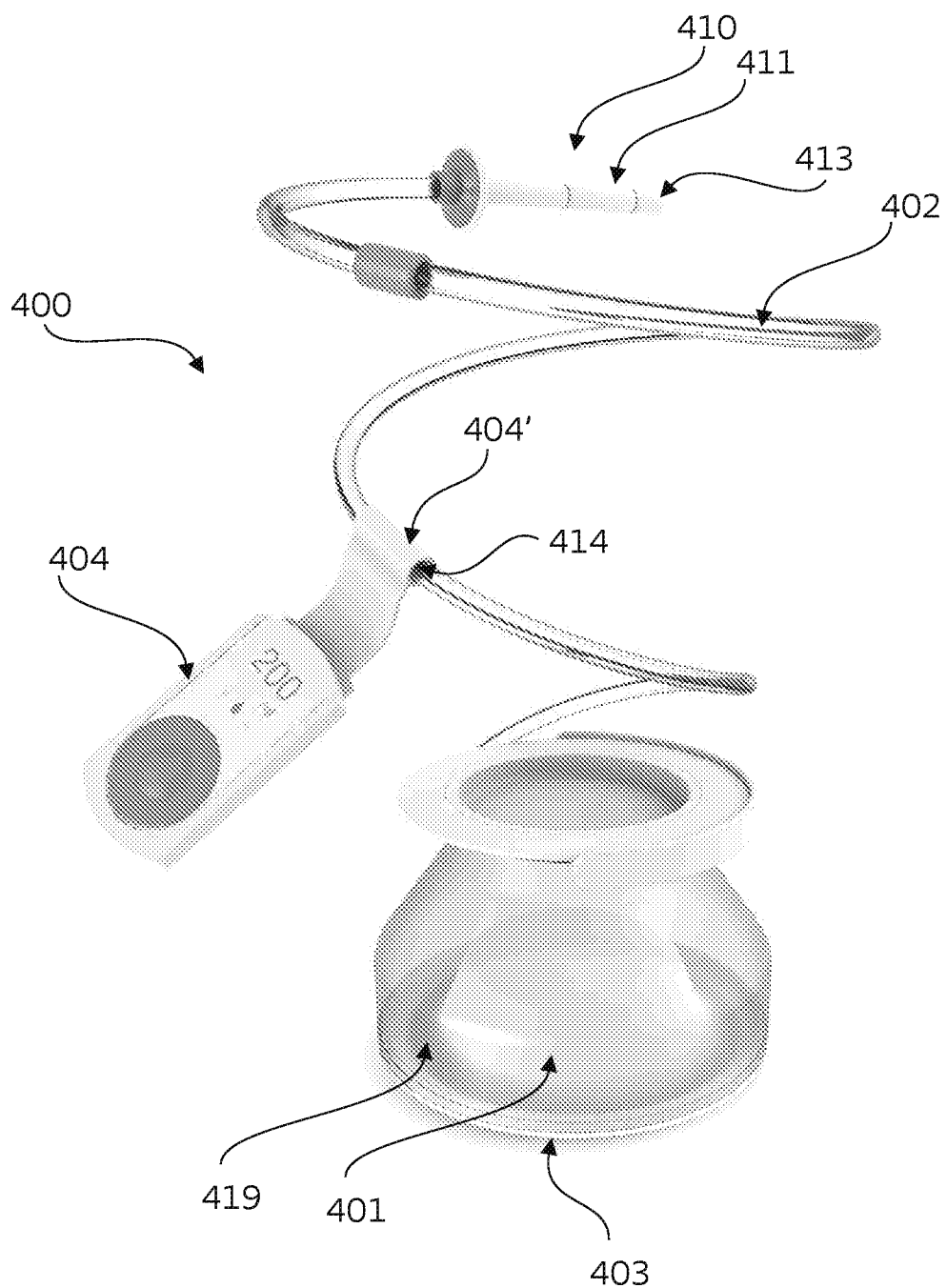
FIG. 7 illustrates one embodiment of a bowel irrigation system.

FIG. 7 illustrates a bowel irrigation system 400. The system 400 comprises a container 401 for holding a liquid, a catheter 410, a tubing 402 connecting the container 401 and the catheter 410, a pump 403 (not shown, but is preferably incorporated in the container, e.g. in the bottom), and a control unit 404 for controlling a flow of fluid in the system 400. The catheter 410 comprises an inflatable balloon 411. The tubing 402 can comprise a first and a second lumen, such that a separate fluid communication can be established between the container 401 and the balloon 411 through the first lumen, and between the container 401 and a proximal end 413 of the catheter 410 through the second lumen. Thereby, liquid held in the container 401 can be pumped selectably into the balloon 410, and through eyelets provided in the proximal end 413 of the catheter 410. By pumping liquid through the eyelets, said liquid irrigates the bowels when the catheter 410 is inserted in the rectum of a user. A liquid sensor 419 for sensing a presence of liquid in the container 401 can be included in the container 401 or be incorporated into the pump 403. A pressure sensor 414 for assessing/measuring the pressure inside the balloon 411 can be arranged at any point between said balloon 411 and the pump 403, provided the pressure sensor 414 is in fluid communication with the interior of the balloon 411. In embodiments, the pressure sensor 414 is arranged by the control unit 404, e.g. by the hinged coupling 404', where the control unit 404 is in communication with the interior of the lumens of the tubing 402, and as such, in fluid communication with the interior of the balloon 411. Thereby, assessing the pressure by the control unit 404 is indicative of the pressure inside the balloon 411. In embodiments, the pressure sensor 414 is arranged in the control unit 404.

Figure 8:
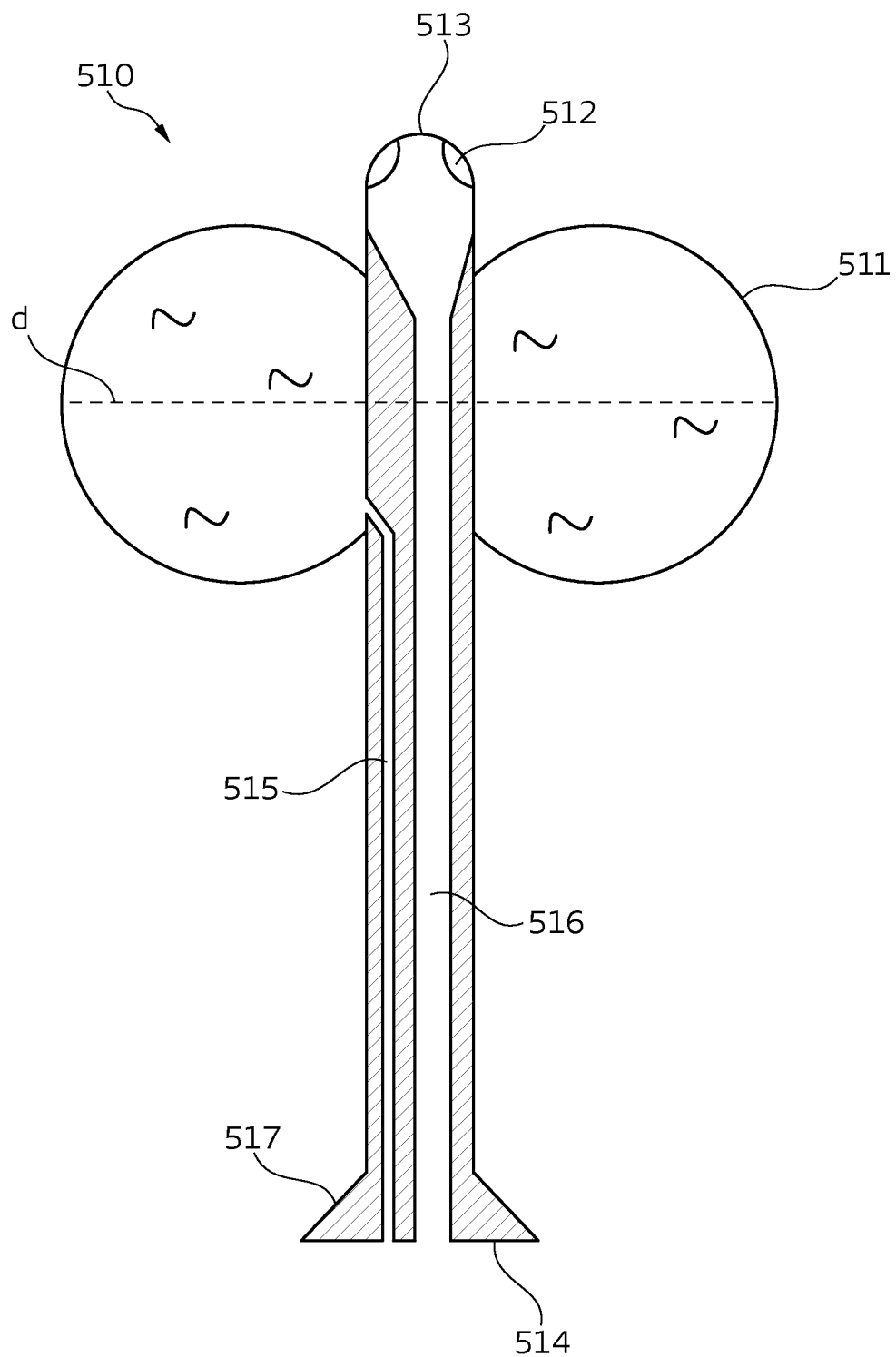
FIG. 8 illustrates a cross-sectional view of one embodiment of a catheter of a bowel irrigation system.

FIG. 8 illustrates a cross-sectional view of a catheter 510 of a bowel irrigation system. The catheter 510 comprises a proximal end 513 and a distal end 514. The proximal end 513 is provided with one or more eyelets 512 for facilitating irrigation of the bowels, when the proximal end 513 is inserted into the rectum of a user. The distal end 514 is provided with a connector 517 for connecting the catheter 510 to a tubing (not shown). The catheter 510 comprises an inflatable balloon 511. The balloon 511 encircles the catheter 510. In embodiments, the inflated balloon 511 is toroidal, i.e. resembles a torus. The diameter d of the balloon 510 can be measured as indicated, the diameter being the external diameter of the torus. The balloon 511 is inflatable by a liquid, e.g. liquid pumped from a container of the bowel irrigation system through the tubing. The catheter 510 comprises two channels; an inflation channel 515 and an irrigation channel 516. The channels can be in separate fluid communication with the container. The inflation channel 515 facilitates communication between the interior of the balloon 511 and the container of the bowel irrigation system, such that the balloon 511 can be inflated by liquid from the container. The irrigation channel 516 facilitates communication between the eyelets 512 of the proximal end 513 and the container of the bowel irrigation system, such that liquid can be pumped through the eyelets 512 and thereby facilitate irrigation of the bowels in a use situation. The balloon 511 is made of a flexible/elastic material for allowing a tight fit around the catheter in a non-inflated state, and for a flexible balloon in an inflated state. Thus, in a non-inflated state, the material of the balloon 511 wraps tightly around the catheter 510. Thereby, no creases are formed when the balloon is not inflated. A pressure sensor in fluid communication with the interior of the balloon 511 can be included in the catheter 510 for assessing the pressure inside the balloon 511.

Although particular features have been shown and described, it will be understood that they are not intended to limit the claimed invention, and it will be made obvious to those skilled in the art that various changes and modifications may be made without departing from the spirit and scope of the claimed invention. Accordingly, the specification and drawings are to be regarded in an illustrative rather than restrictive sense. The claimed invention is intended to cover all alternatives, modifications, and equivalents.

In an embodiment, a system for inflating an inflatable balloon of a catheter for a bowel irrigation system is provided, the system comprising: a container adapted for containing a liquid; a catheter adapted for insertion into a rectum of a user, the catheter comprising an inflatable balloon; a tubing connecting the container and the catheter, a pump adapted for pumping liquid from the container to the balloon through the tubing; a control unit comprising a processor, and a pressure sensor in fluid communication with an interior of the inflatable balloon; wherein the system further comprises:
an amount of liquid contained in the container for inflating the balloon, and
wherein the control unit is configured to control an inflation process by means of a feedback loop comprising the steps of: (i) inflating the balloon by a predefined amount of liquid by means of the pump, (ii) assessing a static pressure inside the balloon by means of the pressure sensor, and (iii) in accordance with the static pressure being below a first threshold, restarting the feedback loop; or, in accordance with the static pressure being above the first threshold, reassessing the static pressure and, in accordance with the reassessed static pressure being above the first threshold, terminating the inflation process; or in accordance with the reassessed static pressure being below the first threshold, restarting the feedback loop.

EMBODIMENTS

Embodiments of the present disclosure are set out in the following items:

1. A system for inflating an inflatable balloon of a catheter for a bowel irrigation system, the system comprising:
    a container adapted for containing a liquid;
    a catheter adapted for insertion into a rectum of a user, the catheter comprising an inflatable balloon;
    a tubing connecting the container and the catheter,
    a pump adapted for pumping liquid from the container to the balloon through the tubing;
    a control unit comprising a processor, and
    a pressure sensor in fluid communication with an interior of the inflatable balloon;
    wherein the system further comprises:
    an amount of liquid contained in the container for inflating the balloon, and
    means for initiating an inflation process comprising a feedback loop comprising the steps of:
       (i) inflating the balloon by a predefined amount of liquid by means of the pump,
       (ii) assessing a static pressure inside the balloon by means of the pressure sensor, and
       (iii) selecting an output by means of the processor based on the static pressure as assessed according to step (ii), the output being selected from:
          restarting the feedback loop according to step (i),
          skipping step (i) and proceeding to assessing the static pressure according to step (ii), and
          terminating the feedback loop.
2. The system according to item 1, wherein the system is adapted for receiving a specification of a maximum volume, and wherein the system comprises means for determining a current volume in the balloon during step (ii) of the feedback loop in addition to assessing a static pressure inside the balloon.
3. The system according to item 2, wherein the processor is adapted for comparing the current volume in the balloon with the maximum volume and for selecting the output of terminating the feedback loop if the current volume has reached the maximum volume.
4. The system according to any one of items 1-3, wherein the processor is adapted for selecting the output of restarting the feedback loop in step (iii) in the first loop of the feedback loop, thereby establishing two consecutively assessed static pressures.
5. The system according to item 4, wherein the processor is adapted for calculating a difference between two consecutively assessed static pressures.
6. The system according to item 5, wherein the processor is adapted to select an output based on the assessed static pressure of the current loop and the difference between two consecutively assessed static pressures.
7. The system according to item 6, wherein the processor is adapted for comparing the assessed static pressure of the current loop with a first threshold value, and/or for comparing the difference between two consecutively assessed static pressures with a second threshold value, and wherein the processor is adapted for selecting the output of restarting the feedback loop if said assessed static pressure of the current loop is below or equal to the first threshold value, and/or the difference between two consecutively assessed static pressures is below or equal to the second threshold value.
8. The system according to item 6, wherein the processor is adapted for comparing the assessed static pressure of the current loop with a first threshold value, and/or for comparing the difference between two consecutively assessed static pressures with a second threshold value, and wherein the processor is adapted for selecting the output of terminating the feedback loop if the assessed static pressure of the current loop is above the first threshold value and/or the difference between two consecutively assessed static pressures is above the second threshold value.

9. The system according to item 6, wherein the processor is adapted for comparing the difference between two consecutively assessed static pressures with a second threshold value, and wherein the processor is adapted for selecting the output of skipping step (i) and proceeding to assessing the static pressure according to step (ii) if the difference between two consecutively assessed static pressures is above the second threshold value.

10. The system according to item 9, wherein the processor is adapted for selecting the output of terminating the feedback loop if the difference between two consecutively assessed static pressures is above the second threshold value after reassessing the static pressure.

11. The system according to any one of items 1-10, wherein the pressure sensor is adapted for continuously assessing a pressure inside the balloon during the inflation process.

12. The system according to item 11, wherein the processor is adapted for comparing the assessed pressure inside the balloon with a third threshold value, and wherein the processor is adapted for selecting the output of terminating the feedback loop if the assessed pressure inside the balloon exceeds the third threshold value at any time during the inflation process.

13. The system according to any one of items 1-12, wherein the predefined amount of liquid is nominally 20 ml.

14. The system according to any one of items 1-12, wherein the processor is adapted for reducing the predefined amount of liquid during each loop of the feedback loop.

15. The system according to any one of items 1-12, wherein the predefined amount of liquid is one Nth of the maximum volume, where N is an integer.

The invention claimed is:

1. A method for inflating an inflatable balloon of a catheter for a bowel irrigation system, where the system includes:
   a container adapted for containing a liquid;
   a catheter adapted for insertion by a user into a rectum of the user, the catheter comprising an inflatable balloon;
   a tubing connecting the container and the catheter;
   a pump adapted for pumping the liquid from the container to the inflatable balloon through the tubing;
   a control unit comprising a processor and a user interface;
   a pressure sensor in fluid communication with an interior of the inflatable balloon;
   the method comprising:
   initiating an inflation process in response to inputs provided by the user to the user interface, with the inflation process comprising steps:
     (i) inflating the inflatable balloon with a predefined volume of the liquid,
     (ii) assessing a static pressure inside the inflatable balloon, and
     (iii) generating an output from the processor based on the static pressure as assessed according to step (ii);
   operating a feedback loop with the processor, with the feedback loop comprising steps selected from:
     restarting the inflation process at step (i),
     skipping step (i) and proceeding to assessing the static pressure according to step (ii), and
     terminating the feedback loop; and
   restarting the feedback loop and establishing two consecutively assessed static pressures and calculating with the processor a difference between the two consecutively assessed static pressures and controlling the feedback loop based on a difference between the two consecutively assessed static pressures.

2. The method according to claim 1, the method further comprising:
   presenting to the user through the user interface a range of the predefined volume of the liquid including a predefined maximum volume of the liquid, and
   determining a current volume of the liquid in the inflatable balloon by assessing the static pressure inside the inflatable balloon in step (ii).

3. The method according to claim 2, comprising terminating the feedback loop when the current volume of the liquid in the inflatable balloon is equal to the predefined maximum volume of the liquid.

4. The method according to claim 1, wherein the predefined volume of the liquid is measured as a first threshold value of liquid volume, the method further comprising:
   restarting the feedback loop when the difference between the two consecutively assessed static pressures is below or equal to the first threshold value of liquid volume.

5. The method according to claim 1, the method further comprising:
   presenting to the user through the user interface a target volume of the liquid; and
   terminating the feedback loop when the static pressure inside of the inflatable balloon is equal to the target volume of the liquid.

6. The method according to claim 1, the method further comprising:
   continuously assessing the static pressure inside the inflatable balloon during the steps (i)-(iii).

7. The method of claim 1, further comprising:
   assessing a bowel pressure measured by the catheter after insertion of the catheter by the user into the rectum of the user; and
   calculating a differential pressure measured as a difference between the static pressure inside the inflatable balloon and the bowel pressure.

8. The method of claim 7, further comprising:
   notifying the user with a message displayed on the user interface when the differential pressure is zero.

9. The method of claim 7, further comprising:
   terminating the inflation process when the differential pressure is zero.

10. A method for inflating an inflatable balloon of a catheter for a bowel irrigation system, where the system includes:
    a pump adapted for pumping a liquid from a container to an inflatable balloon through tubing;
    a control unit comprising a processor and a user interface;
    a pressure sensor provided to measure a pressure in the inflatable balloon;
    the method comprising:
    initiating an inflation process in response to inputs provided by the user to the user interface, with the inflation process comprising steps:
      (i) inflating the inflatable balloon with a predefined volume of the liquid,
      (ii) assessing a static pressure inside the inflatable balloon, and
      (iii) generating an output from the processor based on the static pressure as assessed according to step (ii);

operating a feedback loop with the processor, with the feedback loop comprising steps selected from:
restarting the inflation process at step (i),
skipping step (i) and proceeding to assessing the static pressure according to step (ii), and
terminating the feedback loop; and
assessing a bowel pressure within a rectum of the user and calculating a differential pressure measured as a difference between the static pressure inside the inflatable balloon and the bowel pressure within the rectum.

11. The method of claim 10, further comprising:
notifying the user with a message displayed on the user interface when the differential pressure is zero.

12. The method of claim 10, further comprising:
terminating the inflation process when the differential pressure is zero.

* * * * *